US006476038B1

(12) United States Patent
Darrow et al.

(10) Patent No.: US 6,476,038 B1
(45) Date of Patent: Nov. 5, 2002

(54) AMINO SUBSTITUTED PYRAZOLO[1,5,-A]-1, 5-PYRIMIDINES AND PYRAZOLO[1,5-A]-1,3, 5-TRIAZINES

(75) Inventors: James W. Darrow, Wallingford; Stéphane De Lombaert, Madison; Charles Blum, Westbrook; Jennifer Tran, Guilford; Mark Giangiordano, Branford; David Andrew Griffith, Old Saybrook; Philip Albert Carpino, Groton, all of CT (US)

(73) Assignees: Neurogen Corporation, Branford, CT (US); Pfizer Inc., New York, NY (US)

( * ) Notice: Subject to any disclaimer, the term of this patent is extended or adjusted under 35 U.S.C. 154(b) by 0 days.

(21) Appl. No.: 09/676,972

(22) Filed: Sep. 29, 2000

Related U.S. Application Data

(60) Provisional application No. 60/156,868, filed on Sep. 30, 1999.

(51) Int. Cl.$^7$ .................. C07D 487/04; A61K 31/519; A61P 3/04; A61P 9/12
(52) U.S. Cl. ....................... 514/258; 544/281
(58) Field of Search ............... 544/281; 514/258

(56) References Cited

FOREIGN PATENT DOCUMENTS

WO          9803510        1/1998

OTHER PUBLICATIONS

Raposinho et al. (Endocrinology, vol. 140, No. (9) 4046–4055).*
Cabrele et al. J. of Peptide Sci. 6: 97–122 (2000).*
Oravcova, J., et al., "Drug–Protein Binding Studies: New Trends in Analytical and Experimental Methodology" *Journal of Chromatography B*, vol. 677, pp. 1–28, (1996).
Greene, T.W., et al. "Protective Groups in Organic Synthesis" John Wiley & Sons, pp. 309–405, (1991).

* cited by examiner

*Primary Examiner*—Mark L. Berch
*Assistant Examiner*—H Kahsay Habte
(74) *Attorney, Agent, or Firm*—Ladas & Parry

(57) ABSTRACT

Disclosed are compounds of the formula:

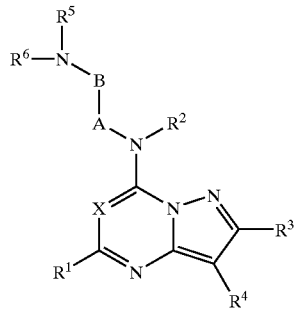

where $R^1$, $R^2$, $R^3$, $R^4$, $R^5$, $R^6$, and X are defined herein. These compounds are selective modulators of NPY1 receptors. These compounds are useful in the treatment of a number of CNS disorders, metabolic disorders, and peripheral disorders, particularly eating disorders and hypertension. Methods of treatment of such disorders and well as packaged pharmaceutical compositions are also provided.

Compounds of the invention are also useful as probes for the localization of NPY1 receptors and as standards in assays for NPY1 receptor binding. Methods of using the compounds in receptor localization studies are given.

31 Claims, No Drawings

AMINO SUBSTITUTED PYRAZOLO[1,5,-A]-1,5-PYRIMIDINES AND PYRAZOLO[1,5-A]-1,3,5-TRIAZINES

RELATED APPLICATION

This application claims priority from provisional application 60/156868 filed on Sep. 30, 1999, which is incorporated herein by reference.

FIELD OF THE INVENTION

This invention relates to certain amino substituted pyrazolo[1,5,-a]-1,5-pyrimidines and pyrazolo[1,5-a]-1,3,5-triazines, preferably those which selectively and/or potently bind mammalian neuropeptide Y (NPY) receptors. This invention also relates to pharmaceutical compositions comprising such compounds. It further relates to the use of such compounds in treating physiological disorders associated with an excess of neuropeptide Y, especially feeding disorders, some psychiatric disorders, and certain cardiovascular diseases.

BACKGROUND OF THE INVENTION

Neuropeptide Y (NPY) is a 36 amino acid peptide first isolated in 1982 and subsequently found to be largely conserved across species. It belongs to a large family of peptides that includes, among others, peptide YY (PYY) and pancreatic peptide (PP). NPY is believed to be the most abundant peptide in the mammalian brain. It is also found in sympathetic neurons, and NPY-containing fibers have been found in peripheral tissues, such as around the arteries in the heart, the respiratory tract, the gastrointestinal tract, and the genitourinary tract. Central injection of NPY elicits a multitude of physiological responses, such as stimulation of feeding, increase in fat storage, elevation of blood sugar and insulin, anxiolytic behaviors, reduction in locomotor activity, hormone release, increase in blood pressure, reduction in body temperature, and catalepsy. In the cardiovascular system, NPY is believed to be involved in the regulation of coronary tone, while in the gastrointestinal tract, PYY is reported to cause inhibition of gastric acid secretion, pancreatic exocrine secretion, and gastroinestinal motility. These effects appear to be selectively mediated by various NPY receptors which currently include the $Y_1$, $Y_2$, $Y_3$, $Y_4$, $Y_5$, and $Y_6$ subtypes, in addition to the hypothetical $Y_1$-like subtype. Selective peptidic agonists and antagonists have been identified for most of the subtypes, but few selective non-peptidic antagonists have been reported. The $Y_1$ and $Y_5$ receptor subtypes appear to be involved in appetite regulation, but their relative contribution to the modulation of food intake and energy expenditure remains unclear. The discovery of non-peptidic antagonists of the $Y_1$ and/or $Y_5$ receptor provides novel therapeutic agents, that are less prone to the shortcomings of the peptide antagonists, namely, for example, poor metabolic stability, low oral bioavailability, and poor brain permeability, for the treatment of obesity and cardiovascular diseases. Recently, a few of such agents have been reported, some of which having demonstrated pharmacological efficacy in pre-clinical animal models. The present invention provides a novel class of potent non-peptidic antagonists of the NPY receptors, in particular, the $Y_1$ receptor.

Insofar as is known, aminoalkyl substituted pyrazolo[1,5,-a]-1,5-pyrimidines and pyrazolo[1,5-a]-1,3,5-triazines have not been previously reported as NPY receptor antagonists useful in the treatment of feeding and cardiovascular disorders. However, this general class of compounds has been described for other uses by virtue of different mechanisms of action, e.g., as antagonists of the corticotropin releasing factor ($CRF_1$). For example International Patent Publication WO 98/03510 describes certain pyraazolotriazines and pyrazolopyrimidines as being of use as corticotropin releasing factors.

SUMMARY OF THE INVENTION

Compounds that interact with the $Y_1$ receptor and inhibit the activity of neuropeptide Y at those receptors are useful in treating physiological disorders associated with an excess of neuropeptide Y, including eating disorders, such as, for example, obesity and bulimia, and certain cardiovascular diseases, for example, hypertension.

This invention relates to a method of treating a physiological disorder associated with an excess of neuropeptide Y, which method comprises administering to a mammal in need of said treatment an effective amount of an amino substituted pyrazolo[1,5,-a]-1,5-pyrimidine or a pyrazolo[1,5-a]-1,3,5-triazine of the formula I:

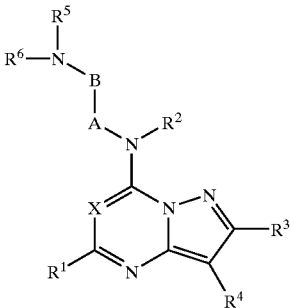

Formula I or a pharmaceutically acceptable salt or prodrug thereof, wherein the compound exhibits a $K_i$ of 5 micromolar or less in an assay of NPY receptor binding, and X is N or $CR^{14}$;

$R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^2$ is
  H,
  $C_1$–$C_6$ alkyl which optionally forms a $C_3$–$C_6$ aminocarbocycle or a $C_2$–$C_5$ aminoheterocycle with A or B, each of which is optionally substituted with $R^7$,
  $C_3$–$C_{10}$ cycloalkyl, or
  ($C_3$–$C_{10}$ cycloalkyl) $C_1$–$C_6$ alkyl; or $R^2$ and $R^6$ jointly form with the 2 nitrogen atoms to which they are bound a $C_2$–$C_5$ aminoheterocycle optionally substituted with $R^7$;

A is $(CH_2)_m$ where m is 1,2 or 3 and is optionally mono- or di-substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halogen, $C_1$–$C_6$ haloalkyl, $OR^7$, $C_1C_6$ alkyl-$OR^7$; $C_1$–$C_6$ cyanoalkyl, $NR^8R^9$, or $C_1$–$C_6$ alkyl-$NR^8R^9$, or A and B jointly form a $C_3$–$C_6$ carbocycle, which is optionally substituted at each carbon atom with $R^7$, or A and $R^2$ jointly form a $C_3$–$C_6$ aminocarbocycle, which is optionally substituted at each carbon atom with $R^7$;

B is $(CH_2)_n$ where n is 0, 1, 2, or 3 and is optionally substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or B and $R^2$ jointly form a $C_3$–$C_6$ aminocarbocycle, which is optionally substituted at each carbon atom with $R^7$, or B and $R^6$ jointly form a $C_3$–$C_6$ aminocarbocycle, which is optionally substituted at each carbon atom with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_2$–$C_6$-alkenyl, $C_2$–$C_6$-alkynyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1C_6$ alkyl-CN, $SO_2NR^8R^9$, $SO_2R^7$, aryl, heteroaryl, heterocycloalkyl, and 3-, 4-, or 5-(2-oxy-1, 3-oxazolidinyl), with the proviso that at least one of the positions ortho or para to the point of attachment of the aryl or heteroaryl ring to the pyrazole is substituted;

$R^5$ and $R^6$ are independently selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, and $C_2$–$C_6$ alkynyl;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each of which is optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that for $SO_2R^7$, $R^7$ cannot be H;

$R^8$ and $R^9$ are independently selected at each occurrence from H, $C_1$–$C_6$ alkyl, $C_3$–$C_1$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN.

Preferred compounds of Formula I exhibit a 20-fold or more greater affinity for the $NPY_1$ receptor than for the $CRF_1$ receptor. Preferred compounds of Formula I also do not exhibit high affinity for the $CRF_1$ receptor.

This invention also encompasses, in additional embodiments, the novel compounds of formula I, and the salts and solvates thereof, as well as pharmaceutical formulations comprising a compound of formula I, or a pharmaceutically acceptable salt or solvate thereof in combination with one or more pharmaceutically acceptable carriers, excipients, or diluents thereof.

This invention also encompasses methods to treat physiological disorders associated with an excess of neuropeptide Y, such as eating and cardiovascular disorders, which method comprises administering to a mammal in need of said treatment an effective amount of a compound of the formula I.

This invention also encompasses methods of selectively inhibiting binding of NPY to $NPY_1$ receptors, which comprises contacting a compound of formula I with neuronal cells, wherein the compound is present in an amount effective to produce a concentration sufficient to inhibit binding of NPY to $NPY_1$ receptors in vitro.

DETAILED DESCRIPTION OF THE INVENTION

The current invention includes a novel group of aminoalkyl substituted 4-amino pyrazolopyrimidines and 7-amino pyrazolo triazines, those of formula I. Preferred aminoalkyl substituted 4-amino pyrazolopyrimidines and 7-amino pyrazolo triazines bind with high affinity to the $NPY_1$ receptor and more preferably act as antagonists of NPY binding to the $NPY_1$ receptor. Preferred compounds of the invention bind with high selectivity to the $NPY_1$ receptor, particulary such compounds do not bind with high affinity to $CRF_1$ receptors. Without wishing to be bound to any particular theory, it is believed that the interaction of the compounds of Formula I with the NPY1 receptor results in the pharmaceutical utility of these compounds.

The invention further comprises methods of treating patients in need of such treatment with an amount of a compound of the invention sufficient to alter the symptoms of a eating disorder or cardiovascular disorder.

The present invention also pertains to methods of inhibiting the binding of NPY receptor ligands, such as NPY or PYY, to the $NPY_1$ receptors which methods involve contacting a compound of the invention with cells expressing $NPY_1$ receptors, wherein the compound is present at a concentration sufficient to inhibit the binding of NPY receptor Ligands to $NPY_1$ receptors in vitro. This method includes inhibiting the binding of NPY receptor ligands to $NPY_1$ receptors in vivo, e.g., in a patient given an amount of a compound of Formula I that would be sufficient to inhibit the binding of NPY receptor ligands to NPY receptors in vitro. The amount of a compound that would be sufficient to inhibit the binding of a NPY receptor ligand to the $NPY_1$ receptor may be readily determined via an $NPY_1$ receptor binding assay, such as the assay described in Example 94A. The $NPY_1$ receptors used to determine in vitro binding may be obtained from a variety of sources, for example from preparations of rat brain or from cells expressing cloned human $NPY_1$ receptors.

The present invention also pertains to methods for altering the signal-transducing activity of NPY1 nreceptors, said method comprising exposing cells expressing such receptors to an effective amount of a compound of the invention. This method includes altering the signal-transducing activity of NPY1 receptors in vivo, e.g., in a patient given an amount of a compound of Formula I that would be sufficient to alter the signal-transducing activity of NPY1 receptors in vitro. The amount of a compound that would be sufficient to alter the signal-transducing activity of NPY1 receptors may be determined via a NPY1 receptor signal transduction assay, such as the assay described in Example 93B.

The NPY1 receptor ligands provided by this invention and labeled derivatives thereof are also useful as standards and reagents in determining the ability of a potential pharmaceutical to bind to the NPY1 receptor.

Radiolabeled derivatives the NPY1 receptor ligands provided by this invention are also useful for mapping the location of NPY1 receptors (e.g., in tissue sections via autoradiography) and as radiotracers for positron emission tomography (PET) imaging, single photon emission computerized tomography (SPECT), and the like, to characterize such receptors in living subjects.

In addition to compounds of Formula I, the invention also provides as preferred compounds, compounds of Formula I wherein X is N or CH; and $R^1$ is H, $C_1$–$C_6$ alkyl, $C_3$–$C_{10}$ cycloalkyl, or ($C_3$–$C_{10}$ cycloalkyl) $C_1$–$C_6$ alkyl. Such compounds will be referred to as compounds of Formula Ia.

Other preferred compounds of Formula I are those compounds wherein

X is N or CH; $R^1$ is $C_1$–$C_6$ alkyl; $R^2$ is H or $C_1$–$C_6$ alkyl; and $R^3$ is $C_1$–$C_6$ alkyl, trifluoromethyl, or $C_1$–$C_6$alkyl-O $C_1$–$C_6$alkyl. Such compounds will be referred to as compounds of Formula Ib.

In another embodiment the invention provides compounds of Formula I, wherein

X is N or CH; $R^1$ is H, $C_1$–$C_6$ alkyl, $C_3$–$C_{10}$ cycloalkyl, or ($C_3$–$C_{10}$ cycloalkyl) $C_1$–$C_6$ alkyl;

$R^2$ is H or $C_1$–$C_6$ alkyl; $R^3$ is $C_1$–$C_6$ alkyl, trifluoromethyl, or $C_1$–$C_6$alkyl-O $C_1$–$C_6$alkyl; and $R^5$ is H. Such compounds will be referred to as compounds of Formula Ic.

Further provided are compounds wherein:

X is N or CH; $R^1$ is $C_1$–$C_6$ alkyl; $R^2$ is H or $C_1$–$C_6$ alkyl; $R^3$ is $C_1$–$C_6$ alkyl, trifluoromethyl, or $C_1$–$C_6$alkyl-O $C_1$–$C_6$alkyl; $R^4$ is phenyl, mono-, di-, or tri-substituted $C_1$–$C_6$ alkyl, $C_3$–$C_{10}$ cycloalkyl, $C_3$–$C_{10}$ cycloalkenyl, ($C_3$–$C_{10}$ cycloalkyl) $C_{1-C6}$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted; and $R^7$, $R^8$, and $R^9$ are as defined for Formula I. Such compounds will be referred to as compounds of Formula Id.

In yet another embodiment the invention provides compounds of Formula I wherein X is N or CH; $R^1$ is $C_{1-C6}$ alkyl; $R^2$ is H or $C_1$–$C_6$ alkyl; $R^3$ is $C_1$–$C_6$ alkyl, trifluoromethyl, or $C_1$–$C_6$ alkyl-O $C_1$–$C_6$alkyl; and $R^4$ is phenyl, mono-, di-, or trisubstituted with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted; $R^5$ is H; and $R^6$ is H, $C_1$–$C_6$ alkyl, $C_3$–$C_{10}$ cycloalkyl, or ($C_3$–$C_{10}$ cycloalkyl) $C_1$–$C_6$ alkyl. Such compounds will be referred to as compounds of Formula Ie.

Additionally the invention provides compounds of Formula I wherein X is N or CH; $R^1$ is $C_1$–$C_6$ alkyl; $R^2$ is H or $C_1$–$C_6$ alkyl; $R^3$ is $C_1$–$C_6$ alkyl, trifluoromethyl, or $C_1$–$C_6$alkyl-O $C_1$–$C_6$alkyl; and $R^4$ is phenyl, mono-, di-, or trisubstituted with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted; and $R^6$ is H, $C_1$–$C_6$ alkyl, $C_3$–$C_{10}$ cycloalkyl, or ($C_3$–$C_{10}$ cycloalkyl) $C_1$–$C_6$ alkyl. Such compounds will be referred to as compounds of Formula If.

Particularly preferred are compounds of Formula I wherein $R^5$ is H, and $R^6$ is cycloalkyl or (cycloalkyl)alkyl. (Compounds of Formula Ig)

For each of Formula Ia-Ig compounds that exhibits a $K_i$ of 5 micromolar or less in an assay of NPY receptor binding are preferred. Also preferred are compounds of Formula I, and Formula Ia-Ig that do not exhibit a Ki or $IC_{50}$ of 5 micromolar or less, or more preferably that do not exhibit a Ki or $IC_{50}$ of 1 micromolar or less, for the CRF1 receptor in an assay of CRF1 receptor binding. An assay of CRF receptor binding is given in Example 94.

In certain situations, the compounds of formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by formula I, include, but are not limited to the compounds in Examples 1-87 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-COOH where n is 0–4, and the like. Those skilled in the art will recognize a wide variety of non-toxic pharmaceutically acceptable addition salts.

The present invention also encompasses the acylated prodrugs of the compounds of formula I. "Prodrugs" are considered to be any covalently bonded carriers which release the active parent drug of formula I in vivo when such prodrug is administered to a mammalian subject. Prodrugs of the compounds of the invention are prepared by modifying functional groups present in the compounds in such a way that the modifications are cleaved, either in routine manipulation or in vivo to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol and amine functional groups in the compounds of formula I; and the like. Those skilled in the art will recognize various synthetic methodologies which may be employed to prepare non-toxic pharmaceutically acceptable addition salts and acylated prodrugs of the compounds encompassed by formula I.

Where a compound exists in various tautomeric forms, the invention is not limited to any one of the specific tautomers. The invention includes all tautomeric forms of a compound.

By "heteroatom" in the present invention is meant oxygen or sulfur, or a nitrogen atom optionally substituted by $C_1$–$C_6$ lower alkyl, $C_1$–$C_6$ arylalkyl, $C_1$–$C_{10}$ cycloalkyl, $C_3$–$C_{10}$ cycloalkyl) $C_1$–$C_6$ alkyl, $C_2$–$C_8$ alkanoyl, $C_1$–$C_6$ sulfonyl.

By "alkyl", "lower alkyl", or "$C_1$–$C_6$ alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "cycloalkyl", or "$C_3$–$C_{10}$ cycloalkyl" in the present invention is meant alkyl groups having 3–10 carbon atoms forming a mono-, bi-, or polycyclic ring system, such as, for example, cyclopropyl, cyclobutyl, cyclopentyl, cyclohexyl, cycloheptyl, norbornyl, and the like.

By "(cycloalkyl)alkyl", "lower (cycloalkyl)alkyl", or ($C_3$–$C_{10}$ cycloalkyl) $C_1$–$C_6$ alkyl in the present invention is meant a straight or branched alkyl substituent formed of 1 to 6 carbon atoms attached to a mono-, bi, or polycyclic ring system having 3–10 carbon atoms, such as, for example, cyclopropylmethyl, cyclobutylmethyl, cyclopentylmethyl, cyclohexylmethyl, cycloheptylmethyl, and the like.

The term "$C_2$–$C_6$ alkenyl" in the present invention means hydrocarbon chains having 2 to 6 carbons in a straight or branched arrangement and containing one or more unsaturated carbon-carbon double bonds which may occur in any stable point along the chain, such as, for example, ethenyl, allyl, isopropenyl, and the like.

By "cycloalkenyl" or "$C_3$–$C_{10}$ cycloalkenyl" in the present invention is meant alkyl groups having 3–10 carbon atoms forming a mono-, bi, or polycyclic ring system having 3–10 carbon atoms and containing one or more carbon-carbon double bonds which may occur in any stable point in the ring, such as, for example, cyclopentenyl, cyclohexenyl, or cycloheptenyl.

The term "$C_2$–$C_6$ alkynyl" in the present invention means hydrocarbon chains having 2 to 6 carbons in a straight or branched arrangement and containing one or more unsaturated carbon-carbon triple bonds which may occur in any stable point along the chain, such as, for example, ethynyl, propargyl, and the like.

The term "aryl" in the present invention means a monocyclic or bicyclic aromatic group having preferably 6 to 10 carbon atoms, such as, for example, phenyl or naphthyl.

The term "heteroaryl" in the present invention means an aryl group in which one or more of the ring(s) carbon atoms have been replaced with a heteroatom. Such groups preferably have 4 to 10 carbon atoms and 1 to 4 heteroatoms, such as, for example, pyridyl, pyrimidinyl, triazinyl, imidazolyl, oxazolyl, isoxazolyl, indolyl, pyrrolyl, pyrazolyl, quinolinyl, isoquinolinyl, thiazolyl, benzothiadiazolyl, triazolyl, triazinyl, pyrazinyl, furanyl, thienyl, benzothienyl, benzofuranyl, tetrazolyl.

The term "heterocyclyl", "heterocycle" or "heterocycloalkyl" in the present invention means a saturated or partially saturated heteroaryl group.

By "$C_1$–$C_6$ arylalkyl" or "$C_1$–$C_6$ heteroarylalkyl" in the present invention is meant a branched or straight-chain alkyl group having 1–6 carbon atoms and substituted on one of the carbon atoms by an optionally substituted aryl or heteroaryl ring, such as, for example, benzyl, phenethyl, methylpyridyl, ethylpyridyl, and the like.

By "$C_5$–$C_8$ arylcycloalkyl" in the present invention is meant cycloalkyl groups having 5–8 carbon atoms and fused to an aryl group, such as, for example, 1,2,3,4 tetrahydronaphthalenyl, 2,3-dihydrobenzothienyl, or 2,3-dihydobenzofuranyl.

By "$C_5$–$C_8$ heteroarylcycloalkyl" in the present invention is meant cycloalkyl groups having 5–8 carbon atoms fused to a heteroaryl group, such as, for example, 1,2,3,4 tetrahydroquinolyl, 2,3-dihydrobenzothienyl, 2,3-dihydobenzofuranyl, or indolinyl.

By "alkoxy", "$C_1$–$C_6$ alkoxy", or "$C_1$–$C_6$ alkyloxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "cycloalkoxy", "$C_3$–$C_{10}$ cycloalkoxy", or "$C_3$–$C_{10}$ cycloalkyloxy" in the present invention is meant a group formed by an oxygen atom attached to a mono-, bi, or polycyclic ring system having 3–10 carbon atoms, such as, for example, cyclopropoxy, cyclobutoxy, cyclopentoxy, cyclohexoxy, or cycloheptoxy.

By "(cycloalkyl)alkyloxy", "($C_3$–$C_{10}$ cycloalkyl) $C_1$–$C_6$ alkoxy", or "($C_3$–$C_{10}$ cycloalkyl) $C_1$–$C_6$ alkyloxy" in the present invention is meant a group formed by an oxygen atom attached to a 1–6 carbon chain linked to a mono-, bi, or polycyclic ring system having 3–10 carbon atoms, such as, for example, cyclopropylmethyloxy, cyclobutylmethyloxy, cyclopentylmethyloxy, cyclohexylmethyloxy, cycloheptylmethyloxy, and the like.

By "$C_3$–$C_6$ aminocarbocycle" is meant a cyclic amino group formed by a nitrogen contained in a ring having 3 to 6 carbon atoms, such as, for example, azetidino, pyrrolidino, piperidino, perhydroazepino.

By "$C_2$–$C_5$ aminoheterocycle" is meant a cyclic amino group formed by a nitrogen contained in a ring having 2 to 5 carbon atoms and one other heteroatom, such as, for example, morpholino, thiomorpholino, piperazino.

By the terms "halo" or "halogen" in the present invention is meant fluoro, chloro, bromo, and iodo.

"Haloalkyl" is intended to include both branched and straight-chain alkyl having the specified number of carbon atoms substituted with 1 or more halogens.

The term "$C_2$–$C_8$ alkanoyl" means an acyl group with 2 to 8 carbon atoms in a linear, branched, or $C_3$–$C_{10}$ cycloalkyl arrangement, optionally substituted with 1 to 5 substituents independently selected at each occurrence from halogen, trifluoromethyl, $OR^7$, $NR^8R^9$, $CONR^8R^9$, $COOR^7$, or CN.

The term "$C_1$–$C_6$ alkyl sulfonyl" means an alkylsulfonyl group containing 1 to 6 carbon atoms in a linear, branched, or $C_3$–$C_7$ cycloalkyl arrangement.

The term "substituted" means that one or more hydrogen on the designated atom is replaced by the specified group, provided that the valence on the designated atom is not exceeded, and that a chemically stable compound results from the substitution.

A stable compound is defined herein as one that can be isolated, characterized, and tested for biological activity.

The term "oxo" (i.e. =O) indicates that two germinal hydrogen atoms are replaced by a double-bond oxygen group.

The term "hydroximino" (i.e. =N—OH) ) indicates that two germinal hydrogen atoms are replaced by a double-bond nitrogen atom substituted with a hydroxyl group.

The term "$C_1$–$C_6$ alkoximino" (i.e. =N—O-Alkyl) indicates that two germinal hydrogen atoms are replaced by a double-bond nitrogen atom substituted with a $C_1$–$C_2$ alkoxy group, such as, for example, methoximino (=N—OMe).

In the present invention, the term "potent" in the context of NPY1 receptor antagonists qualifies a binding affinity with a Ki of less than 10 micromolar, preferably less than 1 micromolar, and more preferably less than 100 nanomolar in the human NPY1 binding assay.

In the present invention, the term "selective" in the context of NPY1 receptor antagonists qualifies a binding affinity with a Ki in the human NPY1 binding assay that is 10-fold or 20-fold, preferably 100-fold, and more preferably 1000-fold, less than the Ki of the same compound measured in another receptor binding assay, in particular the $NPY_5$ and $CRF1_1$ receptor binding assays. Binding assays for the $NPY_5$ and $CRF1_1$ receptors have been described, for example, in *J. Clin. Invest.*, 102, 2136 (1998) and in *Endocrinology* 116, 1653 (1985), respectively. A CRF1 receptor binding assay is also given in Example 94.

As the compounds of formula I are selective antagonists of the Y1 receptor, they are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present locally. These physiological disorders may include: disorders or diseases pertaining to the heart, blood vessels or the renal system, such as vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport, or renal failure; conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia; conditions related to pain or nociception; diseases related to abnormal gastrointestinal motility and secretion, such as different forms of ileus, urinary incontinence, and Crohn's disease; abnormal drink and food intake disorders, such as obesity, anorexia, bulimia, and metabolic disorders; diseases related to sexual dysfunction and reproductive disorders; conditions or disorders associated with inflammation; respiratory diseases, such as asthma and conditions related to asthma and bronchoconstriction; and diseases related to abnormal hormone release, such as leutinizing hormone, growth hormone, insulin, and prolactin.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachid oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle. Dosage levels of the order of from about 0.1 mg to about 50 mg per kilogram of body weight per day are useful in the treatment of the above-indicated conditions (about 0.5 mg to about 3 g per patient per day), although higher amounts, for example up to 140 mg./kg/day may be appropriate in some circumstances. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most eating disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (*Journal of Chromatograpky B* 1996, 677, 1–27).

Compound half-life is inversely proportional to the frequency of dosage of a compound. In vitro half-lives of compounds may be predicted from assays of microsomal half-life as described by Kuhnz and Gieschen (*Drug Metabolism and Disposition* 1998, 26, 1120–1127).

As discussed above, preferred compounds of the invention exhibit good activity in standard in vitro NPY receptor binding assays, specifically the assay as specified in Example 93A, which follows. References herein to "standard in vitro NPY receptor binding assay" are intended to refer to that protocol as defined in Example 93A which follows. Generally preferred compounds of the invention exhibit a $K_i$ of about 1 micromolar or less, still more preferably and $K_i$ of about 100 nanomolar or less even more preferably an $K_i$ of about 10 nanomolar or less or even 1 nanomolar or less in such a defined standard in vitro NPY receptor binding assay as exemplified by Example 93A which follows. In appropriate case, the compounds of the invention may be employed in combination with other active agents. The invention therefore also provides pharmaceutical combination compositions comprising a therapeutically effective amount of a composition comprising: (a) first compound, said first compound being a compound as described above a prodrug thereof, or a pharmaceutically acceptable salt of said compound or of said prodrug; and (b) a second compound, said second compound being a $\beta_3$ agonist, a thyromimetic, an eating behavior modifying agent or a NPY antagonist; and a pharmaceutical carrier, vehicle or diluent. To this end therefore the invention also provides a kit comprising: (a) first compound, said first compound being a compound as described above, a prodrug thereof, or a pharmaceutically acceptable salt of said compound or of said prodrug; (b) a second compound, said second compound being a $\beta_3$ agonist, a thyromimetic, an eating behavior modifying agent or a NPY antagonist; and a pharmaceutical carrier, vehicle, diluent; and (c) means for containing said first and second unit dosage forms wherein the amounts of the first and second compounds result in a therapeutic effect.

Synthetic Schemes

Preparation of Amino Substituted Pyrazolo[1,5,-a]-1,5-Pyrimidines and Pyrazolo[1,5-a]-1,3,5-Triazines Derivatives An illustration of preparation methods of compounds of the present invention is given in the Schemes below. In particular displacement of a leaving group Z, as in formula 10 (Scheme 1) by the appropriate substituted amine provides a method to convert the heterocyclic cores of the present invention, i.e. aryl or heteroaryl substituted pyrazolo[1,5,-a]-1,5-pyrimidines and pyrazo[1,5-a]-1,3,5-triazines, into compounds that potently interact with the NPY1 receptor. Such transformations may require several consecutive chemical steps. Those having skill in the art will recognize that the starting materials may be varied and additional steps employed to produce compounds encompassed by the present invention. The disclosures of all articles and references mentioned in this application, including patents, are incorporated herein by reference. Unless otherwise specified the variable $R^1$, $R^2$, $R^3$, $R^4$, $R^5$, $R^6$, and X are as defined for Formula I.

One general approach is to convert a heterocyclic core A and or a heterocyclic core B

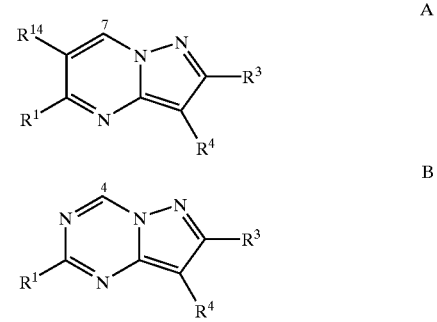

to a compound that exhibits a $K_i$ of 5 micromolar or less in an assay of NPY receptor binding, wherein $R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, and 3-, 4-, or 5-(2-oxo-1,3-oxazolidinyl), with the proviso that at least one of the positions ortho or para to the point of attachment of the aryl or heteroaryl ring to the pyrazole is substituted;

$R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN; by substituting the 7-position of the heterocyclic core A or the 4-position of the heterocyclic core B with a diamine group —N[$R^2$]—A—B—N[$R^6$]—$R^5$ wherein:

$R^2$ is

H, $C_1$–$C_6$ alkyl which optionally forms a $C_3$–$C_6$ aminocarbocycle or a $C_2$–$C_5$ aminoheterocycle with A or B, each of which is optionally substituted with $R^7$, $C_3$–$C_{10}$ cycloalkyl, or ($C_3$–$C_{10}$ cycloalkyl) $C_1$–$C_{10}$ alkyl; or $R^2$ and $R^6$ jointly form with the 2 nitrogen atoms to which they are bound a $C_2$–$C_5$ aminoheterocycle optionally substituted with $R^7$;

A is $(CH_2)_m$ where m is 1,2 or 3 and is optionally mono- or di-substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or A and B jointly form a $C_3$–$C_6$ carbocycle, which is optionally substituted at each carbon atom with $R^7$, or A and $R^2$ jointly form a $C_3$–$C_6$ aminocarbocycle, which is optionally substituted at each carbon atom with $R^7$;

B is $(CH_2)_n$ where n is 0, 1, 2, or 3 and is optionally substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or B and $R^2$ jointly form a $C_3$–$C_6$ aminocarbocycle, which is optionally substituted at each carbon atom with $R^7$, or B and $R^6$ jointly form a $C_3$–$C_6$ aminocarbocycle, which is optionally substituted at each carbon atom with $R^7$;

$R^5$ and $R^6$ are independently selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, and $C_2$–$C_6$ alkynyl;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each of which is optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that for $SO_2R^7$, $R^7$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle; and $R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H. More specifically the following schemes may be used.

SCHEME 1

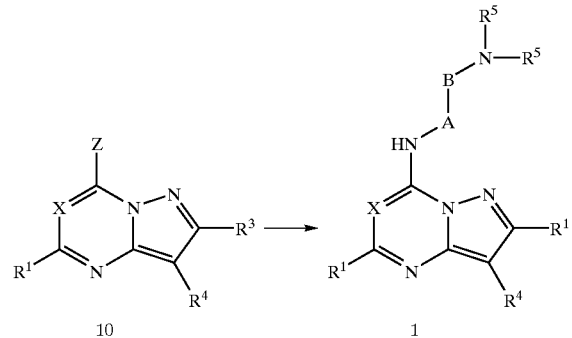

As illustrated in Scheme 1, compounds of formula I can be prepared from intermediate compounds of formula 10, where Z is halogen (preferably chloro or bromo), alkane sulfonyloxy, aryl sulfonyloxy or haloalkane sulfonyloxy, and X, $R^1$, $R^3$ and $R^4$ are defined above, using the procedures outlined below.

Compounds of formula 10 react with an amine of formula $H_2N$—A—B—$N[R^6]$—$R^5$, where A,B, $R^5$ and $R^6$ are defined as above, in the presence or absence of a base in the presence or absence of an inert solvent at reaction temperatures ranging from –78° C. to 250° C. to generate compounds of formula I. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably. lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Preferred reaction temperatures range from 0° C. to 140° C.

SCHEME 2

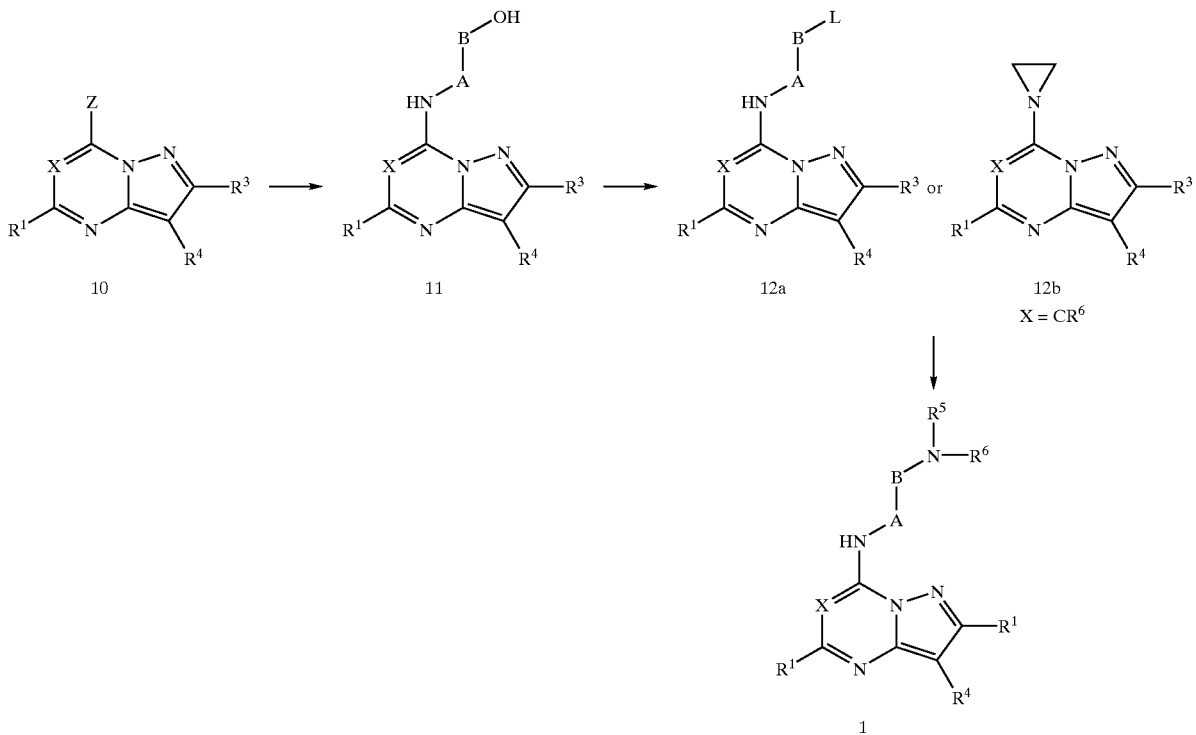

Alternatively, as shown in Scheme 2, compounds of formula I can be obtained by first reacting a compound of formula 10 with an amino alcohol of formula $H_2N$—A—B—OH, where A and B are defined as above, in the presence or absence of a base in the presence or absence of an inert solvent at reaction temperatures ranging from −78° C. to 250° C. to generate intermediates of formula 11. Reacting a compound of formula 11 with a halogenating agent or sulfonylating agent in the presence or absence of a base in the presence or absence of an inert solvent at reaction temperatures ranging from −78° C. to 250° C. to afford products of formula 12a (where Z is halogen, alkane sulfonyloxy, aryl sulfonyloxy or haloalkane sulfonyloxy) or 12b when A and B are both $CH_2$ and X is $CR^{14}$. Halogenating agents include, but are not limited to, $SOCl_2$, $POCl_3$, $PCl_3$, $PCl_5$, $POBr_3$, $PBr_3$, $PBr_5$., $CCl_4/PPh_3$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Preferred reaction temperatures range from −20° C. to 100 C.°C. Compounds of formula 12a or 12b can then be reacted with an amine of formula $HN[R^6]$—$R^5$, where $R^5$ and $R^6$ are defined as above, to give a compound of formula I. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-diisopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Preferred reaction temperatures range from 0° C. to 140° C.

SCHEME 3

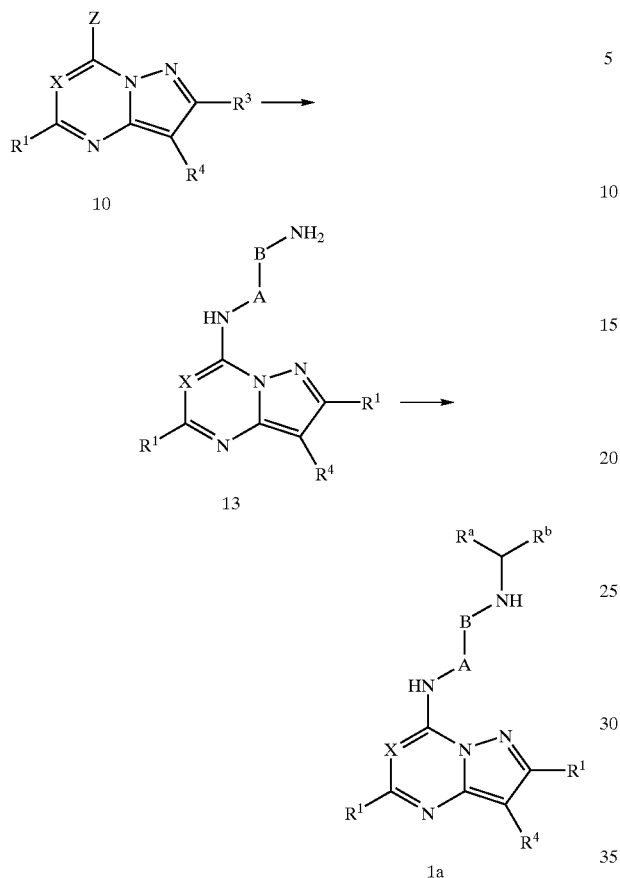

SCHEME 4

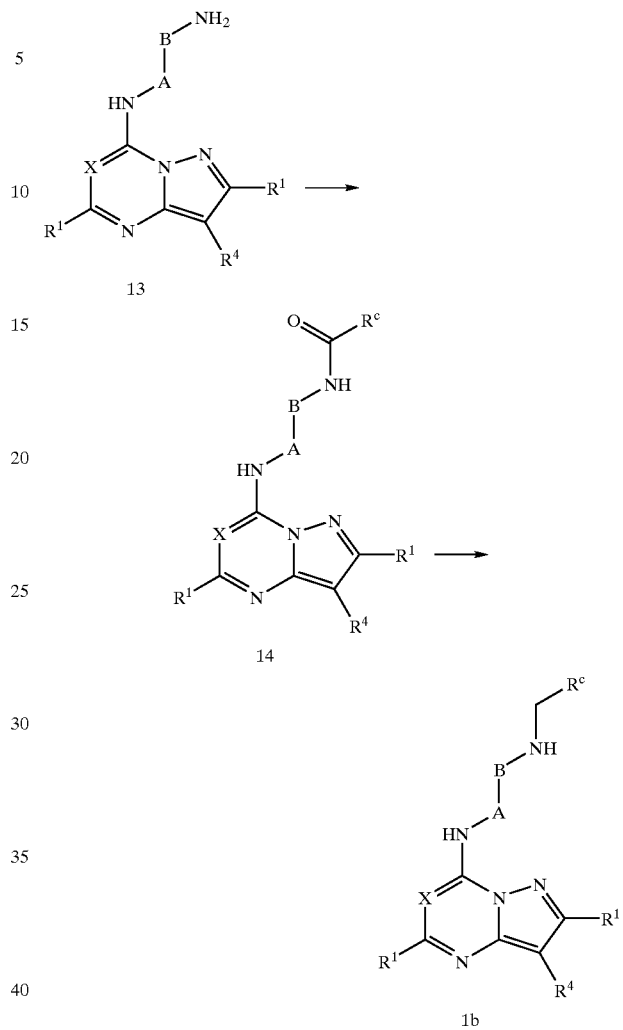

A subset of compounds of formula I, described under formula Ia, can be obtained by first reacting a compound of formula 10 with a diamine of formula $H_2N$—A—B—$NH_2$, where A and B are defined as above, in the presence or absence of a base in the presence or absence of an inert solvent at reaction temperatures ranging from −78° C. to 250° C. to generate intermediates of formula 13. Reaction of a compound of formula 13 with an aldehyde or ketone of Formula $R^a$—C=O—$R^b$ in the presence of a reducing agent provides a compound of formula Ia, where the grouping $R^a$—CH—$R^b$ corresponds to $R^5$ in formula I, as defined above. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene). Preferred reaction temperatures range from −78° C. to 100° C.

Alternatively, a subset of compounds of formula I, described under formula Ib, can be obtained by first reacting a compound of formula 13 with an activated acid of formula $R^c$—C=O—Z, where Z is halo (preferably chloro), O-acyl (preferably O—C=O—$R^c$), in the presence or absence of a base in the presence or absence of an inert solvent at reaction temperatures ranging from −78° C. to 250 ° C. to generate an amide intermediate of formula 14. Reaction of a compound of formula 14 with a reducing agent provides a compound of formula Ib, where the grouping $R^c$—$CH_2$ corresponds to $R^5$ in formula I, as defined above. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or

SCHEME 5

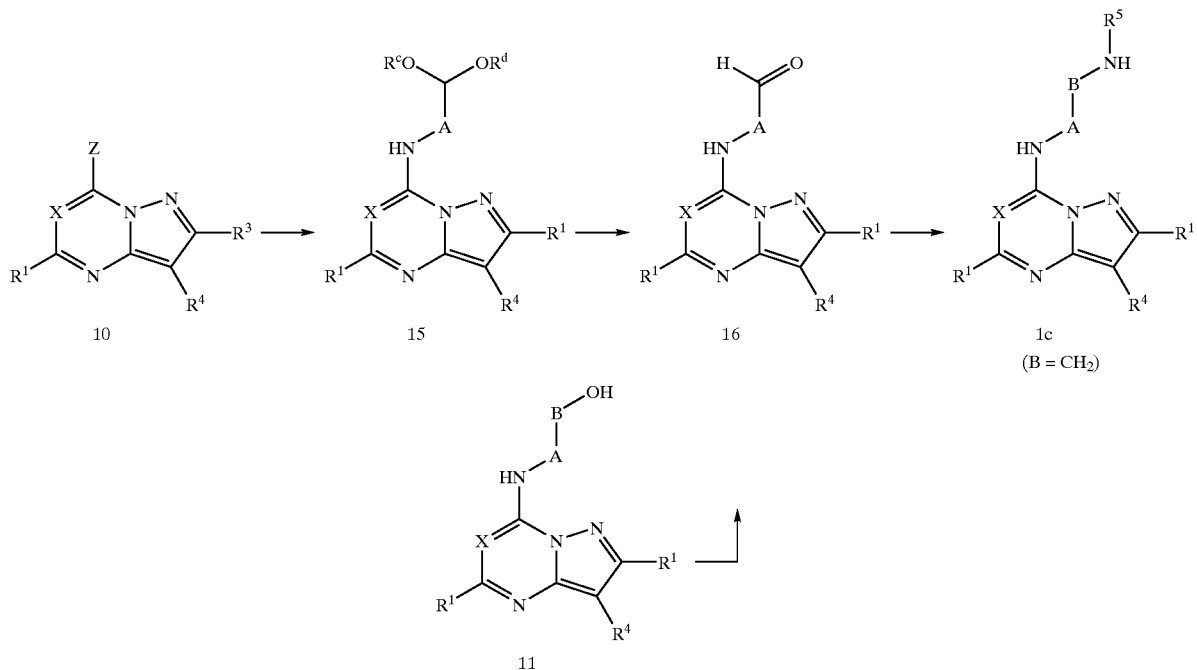

Alternatively, a subset of compounds of formula I, described under formula Ic, can be obtained by first reacting a compound of formula 10 with an amine of formula $H_2N$—A—$CH(OR^c)(OR^d)$, where A is defined above, and $R^c$ and $R^d$ are $C_1$–$C_6$ lower alkyls or, taken together, complete a ketal group, such as, for example a dioxane or dioxolane group, in the presence or absence of a base in the presence or absence of an inert solvent at reaction temperatures ranging from −78° C. to 250° C. to generate compounds of formula 15. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), tri-alkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Compounds of formula 15 react with a protic acid in the presence or absence of an inert solvent at reaction temperatures ranging from −78° C. to 250° C., followed by aqueous work-up to generate compounds of formula 16. Inert solvents may include, but are not limited to dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Protic acids include, but are not limited to, formic acid, acetic acid, trifluoroacetic acid, hydrochloric acid, methane sulfonic acid. Alternatively, compounds of formula 16 can be obtained by oxidation of compounds of formula 11 where B=$CH_2$. Oxidizing agents include, but are not limited to, transition metal oxides, such as $CrO_3$ or $MnO_2$, pyridine-chromium complexes, such as $CrO_3 \cdot C_5H_5N$, pyridinium dichromate or pyridinium chlorochromate, or an oxalyl chloride-DMSO-triethylamine reagent (Swern oxidation). Compounds of formula 16 react with amines of formula $H_2N$—$R^5$, where $R^5$ is defined above, in the presence of a reducing agent in the presence or absence of an inert solvent in the presence or absence of a protic acid at temperatures ranging from −78° C. to 100° C., to give compounds of formula Ic. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethyl amine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene).

SCHEME 6

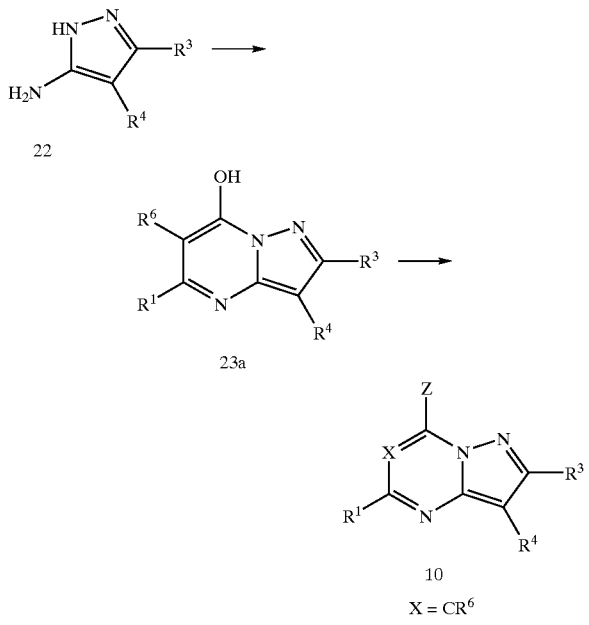

When X is CR[14], as defined above, compounds of formula 10 may be obtained from compounds of formula 22. Compounds of formula 22 can be reacted with compounds of formula $R^1$—C=O—CH($R^{14}$)—C=O—$R^c$, where $R^1$ and $R^{14}$ are defined above, and $R^c$ is halogen, cyano, lower alkoxy (1–6 carbons), or lower alkanoyloxy (1–6 carbons), in the presence or absence of a base in an inert solvent at reaction temperatures ranging from –50° C. to 250° C. to afford compounds of formula 23a. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene). Compounds of formula 23a can then be reacted with a halogenating agent or sulfonylating agent in the presence or absence of a base in the presence or absence of an inert solvent at reaction temperatures ranging from –78° C. to 250° C. to afford products of formula 10 (where Z is halogen, alkane sulfonyloxy, aryl sulfonyloxy or haloalkane sulfonyloxy and X is CR[14]). Halogenating agents include, but are not limited to, $SOCl_2$, $POCl_3$, $PCl_3$, $PCl_5$, $POBr_3$, $PBr_3$, or $PBr_5$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Preferred reaction temperatures range from –20° C. to 100° C.

SCHEME 7

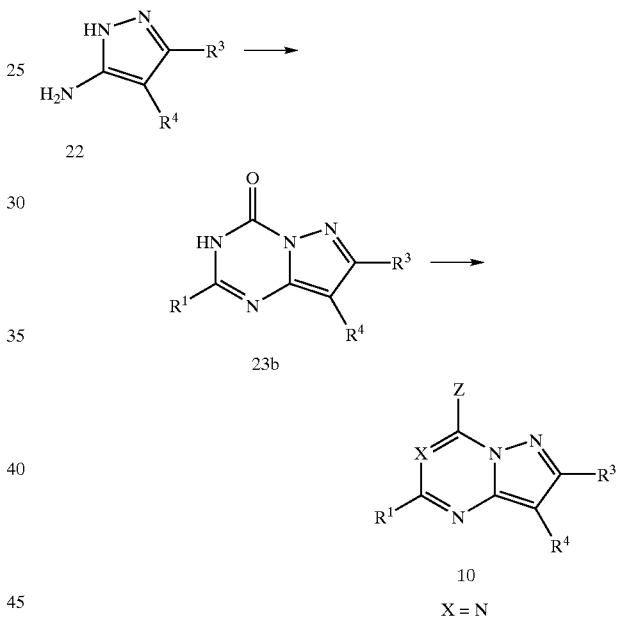

When X is N, compounds of formula 22 can be reacted with compounds of formula $R^1$—C=N(COOR$^g$)—OR$^f$, where $R^1$ is defined above, and $R^g$ is lower alkyl (1–6 carbons), and $R^f$ is halogen, cyano, lower alkoxy (1–6 carbons), or lower alkanoyloxy (1–6 carbons), in the presence or absence of a base in an inert solvent at reaction temperatures ranging from –50° C. to 250° C. to afford compounds of formula 23b. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), heteroaromatic hydrocarbons (preferably pyridine). Compounds of formula 23b can then be reacted with a halogenating agent or sulfonylating agent in the presence or absence of a base in the presence or absence of an inert solvent at reaction temperatures ranging from −78° C. to 250° C. to afford products of formula 10 (where Z is halogen, alkane sulfonyloxy, aryl sulfonyloxy or haloalkane sulfonyloxy and X is N). Halogenating agents include, but are not limited to, $SOCl_2$, $POCl_3$, $PCl_3$, $PCl_5$, $POBr_3$, $PBr_3$, or $PBr_5$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Preferred reaction temperatures range from −20° C. to 100° C.

Alternatively, compounds of formula 23b can be obtained by first reacting compounds of formula 22 with compounds of the formula $R^1$—(C=NH)—$OR^h$, where $R^1$ is defined above and $R^g$ is a lower alkyl group (preferably methyl or ethyl), in the presence or absence of an acid in an inert solvent to give an intermediate of formula 24. Compounds of formula 24 react with a compound of formula $R^i$—C=O—$R^j$, where $R^i$ and $R^j$ are each or independently lower alkoxy (preferably methoxy or ethoxy), 1-imidazolyl, halo, aryloxy (preferably 4-nitrophenoxy) in the presence or absence of an inert solvent to afford compounds of formula 23b. Bases may include, but are not limited to, alkali metals (preferably sodium), alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

SCHEME 8

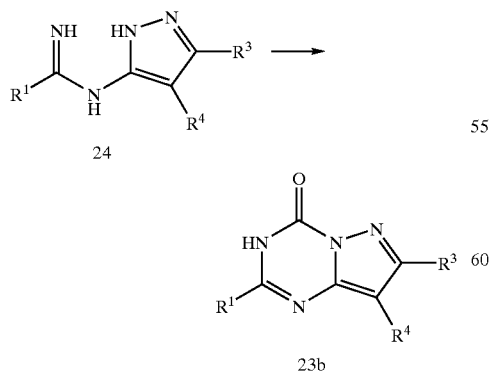

SCHEME 9

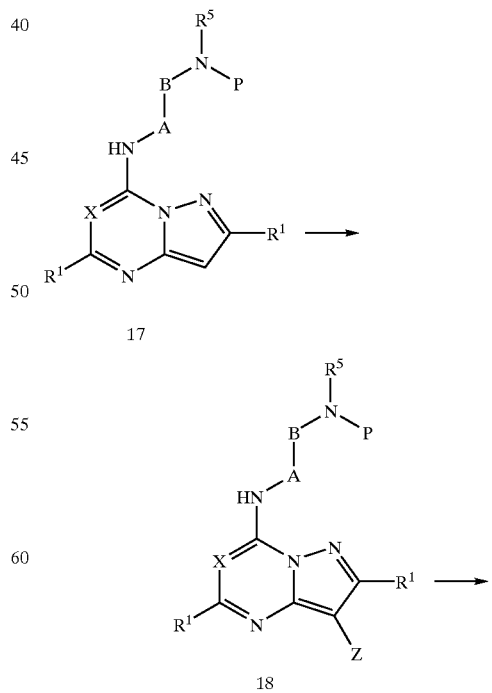

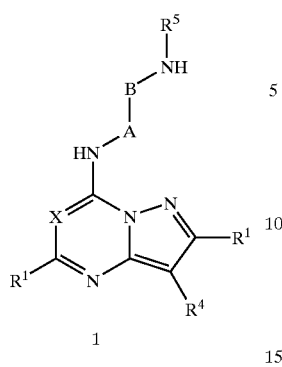

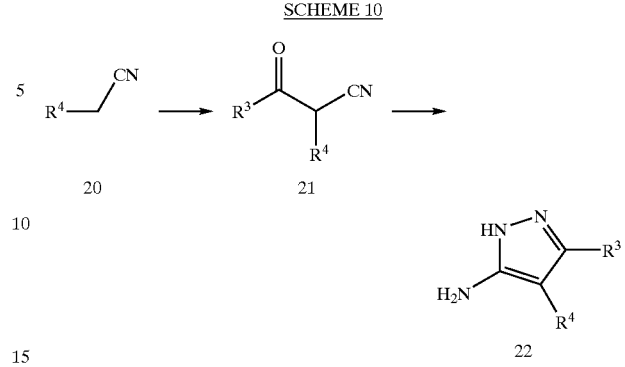

Compounds of formula I can also be prepared from compounds of formula 17 (prepared using the methods applicable to the synthesis of compounds of formula I), where P is H or an appropriate amino protecting group. Such groups, known in the art of organic synthesis for the protection of amines, include those listed in "Protective Groups in Organic Synthesis", by Greene and Wuts [John Wiley & Sons, NY, 1991]. Examples of amine protecting groups include, but are not limited to, acyl types (such as formyl, trifluoroacetyl, phthalyl, and p-toluenesulfonyl), carbamate types (such as benzyloxycarbonyl, t-butoxycarbonyl, 9-fluorenymethyloxycarbonyl, allyloxycarbonyl, and 2,2,2-trichloroethyloxycarbonyl), alkyl types (such as benzyl and triphenylmethyl). Reacting compounds of formula 17 with a halogenating agent provides compounds of formula 18 where X is Br, Cl, or I. Compounds of formula 18 react with a compound of formula $R^4M$ (where M is alkali metal, ZnCl, ZnBr, MgBr, MgCl, MgI, $CeCl_2$, $CeBr_2$, copper halides, $B(OH)_2$, B(O-lower alkyl)$_2$, or Sn(lower alkyl)$_3$) in the presence or absence of an organometallic catalyst in the presence or absence of a base in an inert solvent at temperatures ranging from −100° C. to 200° C. to give compounds of formula I (or their N-protected forms which can then be deprotected). Similar conditions have been described in WO 98/54093. Those skilled in the art will recognize that the reagents $R^4M$ may be generated in situ. Organometallic catalysts include but are not limited to, palladium phosphine complexes (such as $Pd(PPh_3)_4$), palladium halides or alkanoates (such as $PdCl_2(PPh_3)_2$ or $Pd(OAc)_2$), or nickel complexes (such as $NiCl_2(PPh_3)_2$). Bases may include, but are not limited to, alkali metal alkoxides (1–6 carbons) (preferably sodium methoxide, sodium ethoxide, or sodium tert-butoxide), alkali metal carbonates or bicarbonates, alkali metal hydroxides, alkali metal phosphates, or trialkylamines (preferably N,N-di-isopropyl-N-ethyl amine or triethylamine). Inert solvents may include, but are not limited to, lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

Compounds of formula 22 may be obtained from compounds of formula 20, where $R^4$ is defined as above. Compounds of formula 20 are reacted with compounds of formula $R^3$—C=O—$R^c$, where $R^3$ is defined above and $R^c$ is halogen, cyano, lower alkoxy (1–6 carbons), or lower alkanoyloxy (1–6 carbons), in the presence of a base in an inert solvent at reaction temperatures ranging from −78° C. to 200° C. to afford compounds of formula 21. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene). Alternatively, compounds of formula 20 may be reacted with a solvent of formula $R^3$—C=O—$R^c$, where $R^3$ is defined above and $R^c$ is lower alkoxy (1–6 carbons), in the presence of an alkali metal (preferably sodium) at reaction temperatures ranging from −78° C. to 200° C. to afford compounds of forrnula 21. Compounds of formula 21 may be reacted with hydrazine (hydrate or hydrochloride salt) in an inert solvent, at reaction temperatures ranging from 0° C. to 200° C., preferably 70° C. to 150° C., to afford compounds of formula 22. Inert solvents may include, but are not limited to, water, lower alkanoic acids (preferably formic, acetic, or trifluoro acetic acid), alkyl alcohols (1–8 carbons) (preferably methanol or ethanol), lower alkanenitriles (1–6 carbons) (preferably acetonitrile), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

SCHEME 11

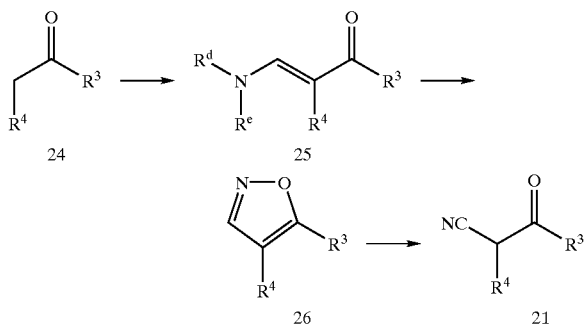

Alternatively, compounds of formula 21 can be obtained by first reacting compounds of formula 24 with dialkyl formamide dialkyl acetal of formula $(R^dR^e)N$—$CH(OR^f)_2$ where $R^d$, $R^e$, and $R^f$ are each or independently $C_1$-$C_6$ lower alkyl (preferably methyl) in the presence or absence of an inert solvent at reaction temperatures ranging from 0° C. to 250° C., preferably between 70 C.°C. and 150° C. to provide compounds of formula 25. Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Compounds of formula 25 can be reacted with hydroxylamine salt (preferably hydrochloride) in the presence or absence of an inert solvent at reaction temperatures ranging from 0° C. to 250° C., preferably between 70° C. and 200° C. to provide oxazoles of formula 26. Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene). Oxazole intermediates of formula 26 can be reacted with a base in the presence or absence of an inert solvent at reaction temperatures ranging from 0° C. to 200° C. Bases may include, but are not limited to, alkali hydroxides (preferably sodium or potassium hydroxide), alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylfornamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

EXAMPLES

The following examples listed in the TABLE are provided to describe the invention in further details. These examples can be prepared by one or more of the above-mentioned method and are intended to illustrate and not to limit the invention.

The numbering system used to describe the compounds of the present invention is as follows:

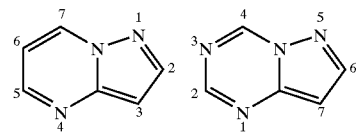

Commercial reagents were used without further purification. THF refers to tetrahydrofuran. LDA refers to lithium diisopropylamide and DBU refers to 1,8-diazabicyclo[5.4.0] undec-7-ene. Room or ambient temperature refers to 20° C. to 25° C. Concentration implies the use of a rotary evaporator. TLC refers to thin layer chromatography. Mass spectral data were obtained either by CI or APCI methods. Other commonly used abbreviations are: Ph is phenyl, Me is methyl, Et is ethyl, Pr is n-propyl, iPr is isopropyl, Bu is butyl, iBu is isobutyl ($CH_2$–$CHMe_2$), tBu is tert-butyl, cBu is cyclobutyl, Pent is n-pentyl, cPent is cyclopentyl, cHex is cyclohexyl, Py is pyridyl, MeOH means methanol, EtOH means ethanol, EtOAc means ethyl acetate, $Et_2O$ means diethyl ether, $CH_2Cl_2$ means methylene chloride, DMSO means dimethyl sulfoxide, NMP means N-methyl pyrrolidone, THF means tetrahydrofuran, DMF means dimethyl formamide, EX means example,

Example 1

Preparation of 7-(2-(cyclohexylamino)ethylamino)-2,5-dimethyl-3-(4-chloro-2,6-dimethylphenyl)-pyrazolo[1,5-a] pyrimidine (formula I where X is CH, $R^1$ is $CH_3$, $R^2$ is H, A is $CH_2$, B is $CH_2$, R3 is $CH_3$, $R^4$ is 2,6-dimethyl-4-chlorophenyl, $R^5$ is cyclohexyl)

A. 4-Bromo-3,5-dimethyl chlorobenzene

Slurry 2,6-dimethyl-4-chloroaniline hydrochloride (23 g, 193.11 g/mol) in $CH_2Cl_2$ (100 ml) and wash with saturated $NaHCO_3$ to generate the free base. Dry over $Na_2SO_4$, filter and evaporate down to a violet oil. Slurry up in 120 mL 6.0 N $H_2SO_4$ and stir vigorously at ambient temperature to break up larger pieces of solid. Cool to 0° C. in an ice/water bath, then portionwise over 15 min add a clear colorless solution of $NaNO_2$ in 50 mL $H_2O$. Maintain temperature 15° C. over course of addition, stirring under dry $N_2$. After 1 hour, carefully pour the cold reaction solution (solution A) into a second solution (solution B) containing 31.7 g CuBr in 33 mL aqueous HBr (48%) at ambient temperature. Let stand at ambient temperature until gas evolution ceases, then heat to 110° C. under $N_2$ while stirring. Stir for 3 h, then cool to rt. Extract the aqueous layer with a (2:1) mixture of hexanes and Et₂O (2×500 mL), then dry the combined organic layers over Na₂SO₄, filter and evaporate down to a brown oil. Triturate the oil with hexanes (100 mL), filter out the remaining solids and wash with copious amounts of hexanes. Evaporate the hexane layers to concentrate then flush through a pad of silica to remove baseline material, using hexanes as eluent. Evaporate to a clear colorless oil (13.5 g).

B. 4-Chloro-2,6-dimethyl benzaldehyde

Dissolve 4-bromo-3,5-dimethyl chlorobenzene (6.5 g) in 50 mL anhydrous THF and cool to −78° C. (dry ice/acetone) under N₂. Dropwise over 5 min add a solution of butyllithium (12.50 mL, 2.5M in hexanes) to the stirring solution of aryl bromide at −78° C. After 2 h, dropwise add anhydrous DMF (5.0 mL) to the orange/red reaction solution and allow to warn to ambient temperature overnight while stirring under N₂. Evaporate the yellow solution down to a yellow oil and partition between H₂O (100 mL) and CH₂Cl₂ (100 mL). Extract the aqueous layer once with CH₂Cl₂, then pool the organic layers and dry over Na₂SO₄, filter and evaporate down to 5.0 g of yellow oil. Use without further purification. LCMS=169.6 (MH⁺).

C. 4-Chloro-2,6-dimethyl benzyl alcohol

Dissolve 4-chloro-2,6-dimethyl benzaldehyde (5.0 g, 168.64 g/mol) in 100 mL dry MeOH. Cool to 0° C. while stirring under N₂. Portionwise add powdered NaBH₄ (0.76 g, 37.85 g/mol) over 5 min. Stir at 0° C. for 2 h, monitoring by TLC until aldehyde consumed, then evaporate to a yellow oil. Add H₂O (50 mL) and bring to pH 7.0 by addition of saturated NH₄Cl. Extract the neutral aqueous layer with CH₂Cl₂ (3×75 mL) and dry the pooled organic layers over Na₂SO₄. Filter and concentrate to a yellow oil. Flush through a pad of silica to remove baseline material, then evaporate to a yellow solid (3.0 g) which can be used without further purification. LCMS=171.6 (MH⁺), 169.6 (M⁻).

D. 4-Chloro-2,6-dimethyl phenyl acetonitrile

Dissolve 4-chloro-2,6-dimethyl benzyl alcohol (2.8 g, 170.66 g/mol) in CH₂Cl₂ (25 mL) and cool to 0° C. under N₂. Dropwise add thionyl chloride (2.4 mL, 3.90 g, 118.9 g/mol) in 10 mL CH₂Cl₂ while stirring under N₂. After 2 h, monitoring by TLC (alcohol Rf=0.35, chloride Rf=1.0; using 20% EtOAc/80% hexanes as eluent), quench the reaction carefully by addition of saturated NaHCO₃ (100 mL) and stir until gas evolution ceases. Separate layers, then extract the aqueous layer with CH₂Cl₂ (100 mL). Pool the organic layers, dry over Na₂SO₄, filter and evaporate to a pale yellow oil. Take up in DMSO (25 mL), add solid NaCN (1.25 g, 49.011 g/mol) and heat to 60° C. while stirring under N₂. Stir 2 h until chloride consumed (TLC; chloride Rf=1.0, nitrile Rf=0.6; using 20% EtOAc/80% hexanes as eluent), then cool to rt. Add 2.0 N NaOH (150 mL) and stir until orange precipitate forms, then filter and wash solid with H₂O. Dissolve solid in CH₂Cl₂, wash with H₂O, the dry over Na₂SO₄. Filter the organic layer and evaporate to an orange oil which crystallizes upon standing at ambient temperature. (2.3 g). LCMS=180.2 (MH⁺), 178.2 (M⁻).

E. 2-(4-Chloro-2,6-dimethylphenyl)-3-oxobutanenitrile

Dissolve 4-chloro-2,6-dimethyl phenyl acetonitrile (2.3 g, 179.2 g/mol) in 15 mL EtOAc and add sodium metal (0.35 g, pea-sized fragments). Heat to reflux (90° C. bath temperature) under N₂ overnight. Evaporate down to solid and slurry up in Et₂O (100 mL); stir vigorously to break up fragments. Filter and wash solid with copious amounts of Et₂O. Dissolve solid in H₂O to form a clear yellow solution, and add 1.0 N HCl (100 mL) to pH 1. Extract the resulting cloudy solution with CH₂Cl₂ (3×100 mL) until aqueous layer is clear. Pool and dry the organic layers over Na₂SO₄, filter and evaporate to yellow oil (1.8 g). TLC: Rf=0.2 using 20% EtOAc/80% hexanes as eluent. LCMS=222.3 (MH⁺); 220.2 (M⁻).

F. 5-Amino-4-(4-chloro-2,6-dimethylphenyl)-3-methylpyrazole

Dissolve anhydrous hydrazine (0.91 g, 0.90 mL) in 20 mL toluene. Add glacial acetic acid (2.25 mL) and allow to stand at ambient temperature for 10 min until solution becomes cloudy white. Add a solution of 2-(4-chloro-2,6-dimethylphenyl)-3-oxobutanenitrile in 10 toluene, rinsing out the ketonitrile flask with an additional 5 mL toluene. Heat to reflux under N₂ (130° C.) with Dean-Stark trap attached. Water will begin to accumulate after 10 min or so. After 2 h, evaporate down and partition between 1.0 N NaOH (100 mL) and EtOAc (100 mL). Extract aqueous layer with EtOAc (2×100 mL), then pool the organic layers and dry over Na₂SO₄. Filter and evaporate to yellow oil (1.75 g). Use without further purification. LCMS=236.5 (MH⁺); 234.5 (M⁻).

G. 7-Hydroxy-2,5-dimethyl-3-(4-chloro-2,6-dimethylphenyl)-pyrazolo[1,5-a]pyrimidine

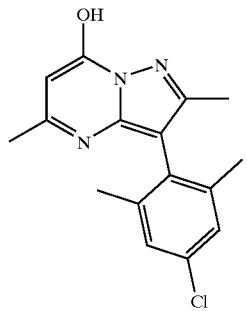

Dissolve 5-amino-4-(4-chloro-2,6-dimethylphenyl)-3-methylpyrazole in 20 mL glacial acetic acid at ambient temperature, and add ethyl acetoacetate (2.0 mL, 1.99 g). Heat to reflux (130° C.) under N₂ overnight. Evaporate down to concentrate and add 200 mL Et2O to precipitate out product. Stir at ambient temperature for 1 hour, then filter and wash the resulting white solid (1.25 g) with copious amounts of Et₂O. LCMS=302.2 (MH⁺); 300.2 (M⁻).

H. 7-Chloro-2,5-dimethyl-3-(4-chloro-2,6-dimethylphenyl)-pyrazolo[1,5-a]pyrimidine

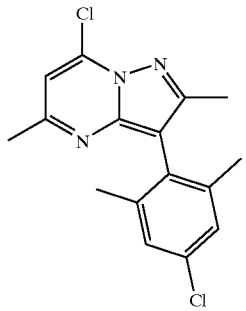

Slurry 7-hydroxy-2,5-dimethyl-3-(4-chloro-2,6-dimethylphenyl)-pyrazolo[1,5-a] pyrimidine in 10 mL POCl$_3$ and reflux at 130° C. under N$_2$. After 2 h, monitoring by TLC (alcohol Rf=0.5, chloride Rf=1.0; EtOAc as eluent), quench the reaction carefully at ambient temperature by diluting with 50 mL CH$_2$Cl$_2$ and pouring slowlyj into non-stirring saturated NaHCO$_3$. Adjust stirring speed to control rate of quenching of residual POCl$_3$ and stir until gas evolution ceases. Separate the layers and extract the aqueous layer with CH$_2$Cl$_2$ (2×50 mL). Pool the organic layers and dry over Na$_2$SO$_4$. Filter and evaporate to yellow oil, which is used directly without further purification.

I. 7-(2-aminoethylamino)-2,5-dimethyl-3-(4-chloro-2,6-dimethylphenyl)-pyrazolo[1,5-a] pyrimidine

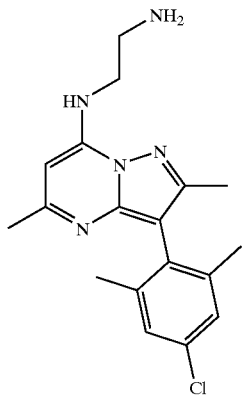

Dissolve 7-chloro-2,5-dimethyl-3-(4-chloro-2,6-dimethylphenyl)-pyrazolo[1,5-a] pyrimidine in 25 mL CH$_3$CN, then add excess ethylenediamine (5 mL) and heat to 80° C. for 3–6 h under N$_2$ with attached reflux condenser. (TLC; product diamine Rf=0.5, aryl chloride Rf=1.0; [10% (2.0M NH$_3$ in MeOH)/90% CH$_2$Cl$_2$] as eluent). Cool to ambient temperature and evaporate to yellow oil. Partition between CH$_2$Cl$_2$ (50 mL) and 1.0 N NaOH (50 mL), and extract aqueous layer 2×30 mL CH$_2$Cl$_2$. Pool organic layers, dry over Na$_2$SO$_4$, filter and evaporate to yellow-white foam (1.25 g). Use without further purification. LCMS=344.4 (MH$^+$); 342.3 (M$^-$).

J. 7-(2-(Cyclohexylamino)ethylamino)-2,5-dimethyl-3-(4-chloro-2,6-dimethylphenyl)-pyrazolo[1,5-a] pyrimidine

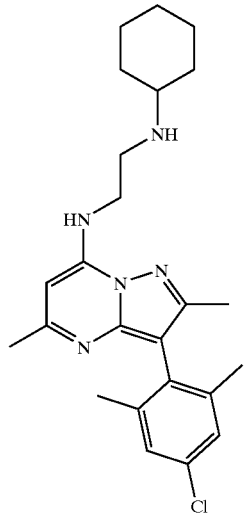

Dissolve 7-(2-aminoethylamino)-2,5-dimethyl-3-(4-chloro-2,6-dimethylphenyl)-pyrazolo [1,5-a] pyrimidine (0.183 g, 5.4×10$^{-4}$ mol, 339.2 g/mol) in dichloroethane (5 mL) and add cyclohexanone (100.12 g/mol) and sodium triacetoxyborohydride (0.172 g, 211.94 g/mol). To the resultant slurry, add glacial acetic acid (0.032 mL, 5.4×10$^{-4}$ mol) and stir at ambient temperature under N$_2$ for 3 h. Partition between CH$_2$Cl$_2$ (3 mL) and 1.0 N NaOH (10 mL), then separate the layers and chromatograph the CH$_2$Cl$_2$ layer using [10% (2.0M NH$_3$ in MeOH)/90% CH$_2$Cl$_2$] as eluent. Obtained 0.16 g white solid-foam upon evaporation.

Example 2

Preparation of 7-(2-cyclopentylamino)ethylamino)-3-(2,4-dimethoxyphenyl)-2,5-dimethyl-pyrazolo[1,5-a]pyrimidine (formula I where X is CH, R$^1$ is CH$_3$, R$^2$ is H, A is CH$_2$, B is CH$_2$, R$^3$ is CH$_3$, R$^4$ is 2,4-dimethoxyphenyl, R$^5$ is cyclopentyl)

A. (3E)-3-(2,4-dimethoxyphenyl)-4-(dimethylamino)but-3-en-2-one

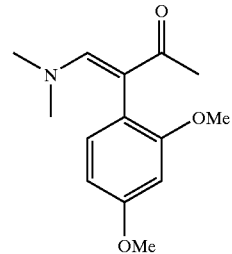

Dissolve 1-(2,4-dimethoxyphenyl)acetone (1.0 g, 5.15 mmol, 194.23 g/mol) in DMF-diethyl acetal (4.5 mL, 25.7 mmol, 147.22 g/mol) and stir under N$_2$ at 100° C. overnight. TLC using 20% EtOAc/80% hexanes; (ketone Rf=0.25, product Rf=0.0). Evaporate to thick oil, dissolve in EtOAc (25 mL) and wash with H$_2$O (3×25 mL). Extract pooled H$_2$O

B. 4-(2,4-Dimethoxyphenyl)-5-methyl-isoxazole

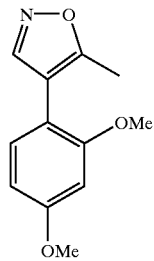

Dissolve (3E)-3-(2,4-dimethoxyphenyl)-4-(dimethylamino)but-3-en-2-one (5.1 g, 20.6 mmol) in EtOH (50 mL) and add NH$_2$OH.HCl (3.05 g, 44.0 mmol). Heat to reflux under N$_2$ for 20 min. Cool and evaporate to red-brown oil. Dissolve in CH$_2$Cl$_2$, dry over Na$_2$SO$_4$, filter and concentrate to red-brown oil (4.4 g). Use without further purification. LCMS=220.2 (MH$^+$); 218.2 (M$^-$).

C. 2-(2,4-Dimethoxyphenyl)-3-oxobutanenitrile

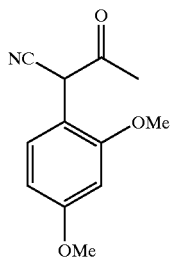

Slurry 4-(2,4-dimethoxyphenyl)-5-methyl-isoxazole (4.4 g) in 1.0 N NaOH (35 mL) and add 35 mL MeOH to dissolve. Heat at 60° C. under N$_2$ for 1 hour, then cool to clear brown solution. Add 1.0 N HCl to acidify to pH 1, then filter the resulting white solid precipitate. Dissolve solid in EtOAc, dry over Na$_2$SO$_4$, filter and concentrate to red oil. Use without further purification. LCMS=220.2 (MH$^+$); 218.2 (M$^-$).

D. 5-Amino-4-(2,4-dimethoxylphenyl)-3-methylpyrazole

This compound was prepared as described in Example 1F.

E. 7-Hydroxy-2,5-dimethyl-3-(2,4-dimethoxyphenyl)-pyrazolo[1,5-a]pyrimidine

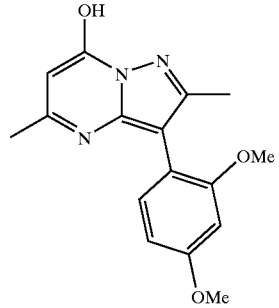

This compound was prepared as described in Example 1G.

F. 7-Chloro-2,5-dimethyl-3-(2,4-dimethoxyphenyl)-pyrazolo[1,5-a]pyrimidine

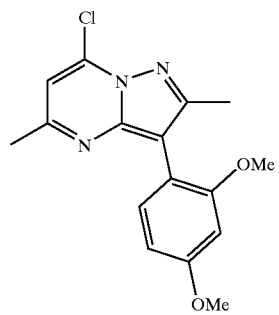

Slurry 7-hydroxy-2,5-dimethyl-3-(2,4-dimethoxyphenyl)-pyrazolo[1,5-a] pyrimidine in 10 mL POCl$_3$ and reflux at 130° C. under N$_2$. After 2 h, monitoring by TLC (alcohol Rf=0.5, chloride Rf=1.0; EtOAc as eluent), quench the reaction carefully at ambient temperature by diluting with 50 mL CH$_2$Cl$_2$ and pouring slowly into non-stirring saturated NaHCO$_3$. Adjust stirring speed to control rate of quenching of residual POCl$_3$ and stir until gas evolution ceases. Separate the layers and extract the aqueous layer with CH$_2$Cl$_2$ (2×50 mL). Pool the organic layers and dry over Na$_2$SO$_4$. Filter and evaporate to yellow oil, which is used directly without further purification.

G. 7-(2-aminoethylamino)-2,5-dimethyl-3-(2,4-dimethoxyphenyl)-pyrazolo[1,5-a] pyrimidine

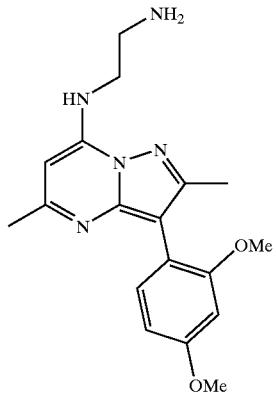

Dissolve 7-chloro-2,5-dimethyl-3-(2,4-dimethoxyphenyl)-pyrazolo[1,5-a] pyrimidine in 25 mL $CH_3CN$, then add excess ethylenediamine (5 mL) and heat to 80° C. for 3–6 h under $N_2$ with attached reflux condenser. (TLC: [10% (2.0M $NH_3$ in MeOH)/90% $CH_2Cl_2$] as eluent). Cool to ambient temperature and evaporate to yellow oil. Partition between $CH_2Cl_2$ (50 mL) and 1.0 N NaOH (50 mL), and extract aqueous layer 2×30 mL $CH_2Cl_2$. Pool organic layers, dry over $Na_2SO_4$, filter and evaporate to yellow-white foam. Use without further purification.

H. 7-(2-cyclopentylamino)ethylamino)-3-(2,4-dimethoxyphenyl)-2,5-dimethyl-pyrazolo[1,5-a] pyrimidine

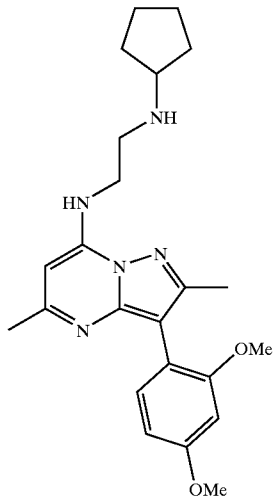

This compound was prepared as described in Example 1J.

Example 3

Preparation of 7-(2-(cyclopentylamino)ethylamino)-2,5-dimethyl-3-(2,6-dimethyl-4-methoxyphenyl)-pyrazolo[1,5-a] pyrimidine (formula I where X is CH, $R^1$ is $CH_3$, $R^2$ is H, A is $CH_2$, B is $CH_2$, $R^3$ is $CH_3$, $R^4$, is 2,4-dimethyl-4-methoxyphenyl, $R^5$ is cyclopentyl)

A. 4-Methoxy-2,6-dimethyl phenyl acetonitrile

Dropwise add a solution of chlorotrimethylsilane (20 mL) in $CH_2Cl_2$ (40 mL) to a stirred solution cooled to 0° C. of 4-methoxy-2,6-dimethyl benzyl alcohol (approx. 74 mmol) in 300 mL $CH_2Cl_2$. Solution changes color from colorless to yellow and then to purple over the course of the reaction. After 2 h, monitoring by TLC (alcohol Rf=0.25, chloride Rf=0.95; using 20% EtOAc/80% hexanes as eluent), evaporate down to a yellow oil. Dissolve in dry DMF (50 mL) and cool to 0° C. under $N_2$. Add freshly ground NaCN (7.0 g) portionwise over 5 minute (exothermic) to the stirring reaction, forming a yellow/white slurry. Stir for 5–8 h at 0° C. until no starting material remains, as determined by TLC (nitrile Rf=0.5; using 20% EtOAc/80% hexanes as eluent). Partition the reaction solution between EtOAc (100 mL) and 0.1 N NaOH (300 mL). Dry the EtOAc layer over Na2SO4, filter and evaporate to yellow oil. Chromatograph in 10% EtOAC/90% hexanes on silica to remove residual chloride and evaporate to 2.1 g yellow solid; clean by TLC. LCMS= 176.5 ($MH^+$), 174.4 ($M^-$).

B. 7-(2-(Cyclopentylamino)ethylamino)-2,5-dimethyl-3-(2,6-dimethyl-4-methoxyphenyl)-pyrazolo[1,5-a] pyrimidine

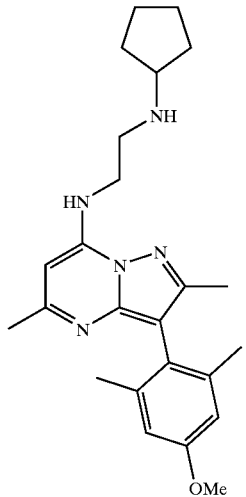

7-(2-(cyclopentylamino)ethylamino)-2,5-dimethyl-3-(2,6-dimethyl-4-methoxyphenyl)-pyrazolo[1,5-a] pyrimidine is obtained from 4-methoxy-2,6-dimethyl phenyl acetonitrile using the procedures described in EXAMPLE 1 E, F, G, H, I, and J.

Example 4

Preparation of 7-(2-(cyclopentylamino)ethylamino)-2-trifluoromethyl-5-methyl-3-(2,4-dichlorophenyl)-pyrazolo[1,5-a] pyrimidine (formula I where X is CH, $R^1$ is $CH_3$, $R^2$ is H, A is $CH_2$, B is $CH_2$, $R^3$ is $CF_3$, $R^4$ is 2,4-dichlorophenyl, $R^5$ is cyclopentyl)

A. 2-(2,4-Dichlorophenyl)-4,4,4-trifluoro-3-oxobutanenitrile

Slurry 2,4-dichlorophenylacetonitrile (I) (5.0 g, 26.9 mmol, 186.04 g/mol) in ethyl trifluoroacetate (6.4 mL, 7.6 g, 142.08 g/mol) and add 20 mL anhydrous THF. Portionwise at ambient temperature add NaH (1.88 g, 47.1 mmol, 60% in mineral oil) over 5 min. Heat reaction to reflux (90° C. bath temperature) overnight. Evaporate to thick red-brown oil and partition between $Et_2O$ (100 mL) and $H_2O$ (60 mL).

Separate layers and extract H₂O with Et₂O (2×75 mL). Acidify the aqueous layer with 1.0 N HCl to pH 1 (becomes cloudy white suspension) and extract aqueous layer with CH₂Cl₂ (3×100 mL). Dry pooled CH₂Cl₂ layers over Na₂SO₄, filter and concentrate to yellow oil (7.5 g, 26.5 mmol). Use without further purification. LCMS=281.9 (MH⁺); 279.8 (M⁻).

B. 7-(2-(Cyclopentylamino)ethylamino)-2-trifluoromethyl-2-methyl-3-(2,4-dichlorophenyl)-pyrazolo[1,5-a] pyrimidine

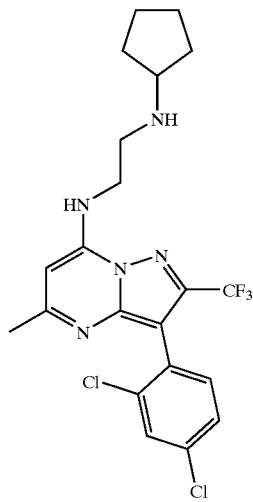

7-(2-(Cyclopentylamino)ethylamino)-2-trifluoromethyl-5-methyl-3-(2,4-dichlorophenyl)-pyrazolo[1,5-a] pyrimidine is obtained from 2-(2,4-dichlorophenyl)-4,4,4-trifluoro-3-oxobutanenitrile using the procedures described in EXAMPLE 1 F, G, H, I, and J.

Example 5

Preparation of 7-(2-(cyclopentylamino)ethylamino)-2,5-dimethyl-3-(4-methoxy-2,6-dimethylphenyl)-[1,5-a]-pyrazolo-1,3,5-triazine (formula I where X is N, R¹ is CH₃, R² is H, A is CH₂, B is CH₂, R³ is CH₃, R⁴ is 2,6-dimethyl-4-methoxyphenyl, R⁵ is cyclopentyl)

A. (Iminoethyl)[4-(4-methoxy-2,6-dimethylphenyl)-3-methylpyrazol-5-yl]amine acetate salt

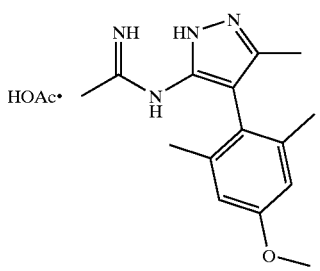

To a solution of 5-amino-4-(4-methoxy-2,6-dimethylphenyl)-3-methylpyrazole (1.89 g) in acetonitrile (30 mL) add ethylacetimidate (free base, 1.8 mL) followed by acetic acid (0.47 mL). Collect the precipitate that formed upon stirring overnight by filtration. Wash the solid with dry ether and dry to afford 2.61 g of (iminoethyl)[4-(4-methoxy-2,6-dimethylphenyl)-3-methylpyrazol-5-yl]amine acetate salt as a white powder.

B. 2,6-Dimethyl-7-(2,6-dimethyl-4-methoxyphenyl)-3H-[1,5-c]-pyrazolo-1,3,5-triazin-4-one

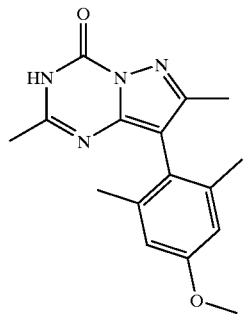

Add sodium pieces (1.81 g) to a flask containing anhydrous ethanol and equipped with a reflux condenser. Allow the mixture to stir until all the sodium is consumed and then add the amidine (2.61 g as the acetate salt) from step A in one portion. Add diethyl carbonate (7.6 mL) and reflux the mixture overnight. Concentrate the mixture under reduced pressure, dissolve the residue in water (75 mL) and adjust the pH to 5 with 3N HCl. Extract the aqueous mixture with EtOAc and wash the extracts with brine, dry over anhydrous sodium sulfate, and concentrate in vacuo to obtain a foam. Stir the residue with hexanes for 20 min and collect the solid by filtration, then wash with hexanes to obtain 2.01 g of 2,6-dimethyl-7-(2,6-dimethyl-4-methoxyphenyl)-3H-[1,5-c]-pyrazolo-1,3,5-triazin-4-one as a yellow powder: MS 299 (M+H).

C. 4-Chloro-2,6-dimethyl-7-(2,6-dimethyl-4-methoxyphenyl) [1,5-a]-pyrazolo-1,3,5-triazine

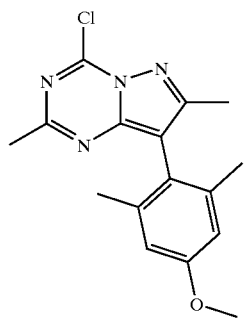

Dissolve 2,6-dimethyl-7-(2,6-dimethyl-4-methoxyphenyl)-3H-[1,5-c]-pyrazolo-1,3,5-triazin-4-one from step B (1 g) in POCl₃ (50 mL) and add N,N-dimethylaniline (0.55 mL). Reflux the reaction mixture under a dry nitrogen atmosphere for 18 h at which time concentrate the mixture under reduced pressure. Dissolve the residue in EtOAc and wash with a saturated aqueous NaHCO₃ solution, then with brine. Dry the organic layer over anhydrous sodium sulfate, filter and concentrate under reduced pressure to obtain 4-chloro-2,6-dimethyl-7-(2,6-dimethyl-4-methoxyphenyl) [1,5-a]-pyrazolo-1,3,5-triazine as a dark oil. MS 317 (M+H).

D. 2,6-Dimethyl-7-(2,6-dimethyl-4-methoxyphenyl)-4-(2-aminoethyl)amino-[1,5-a]-pyrazolo-1,3,5-triazine

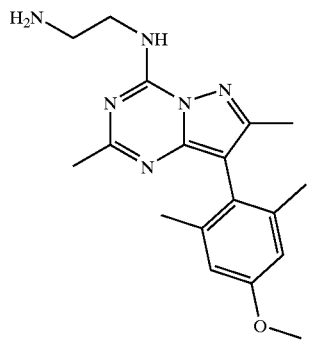

Dissolve 4-chloro-2,6-dimethyl-7-(2,6-dimethyl-4-methoxyphenyl) [1,5-a]-pyrazolo-1,3,5-triazine in dry toluene (10 mL) to form a stock solution of the chloride (~0.34 M). Add a portion of this solution (8 mL) dropwise into a stirring solution of ethylenediamine (3.6 mL) in acetonitrile (50 mL) which is heated to 60° C. After 3 h at 60° C., cool the solution, concentrate under reduced pressure, dilute with 10% NaOH and extract with EtOAc. Wash the combined extracts with brine, dry over anhydrous sodium sulfate and concentrate under reduced pressure to obtain a yellow residue. Triturate the residue with 20% EtOAc/hexanes and collect the resulting solid by filtration to obtain 0.72 g of 2,6-dimethyl-7-(2,6-dimethyl-4-methoxyphenyl)-4-(2-aminoethyl)amino-[1,5-a]-pyrazolo-1,3,5-triazine as a yellow solid: MS 341 (M+H).

E. 7-(2-(Cyclopentylamino)ethylamino)-2,5-dimethyl-3-(4-methoxy-2,6-dimethylphenyl)-[1,5-a]-pyrazolo-1,3,5-triazine

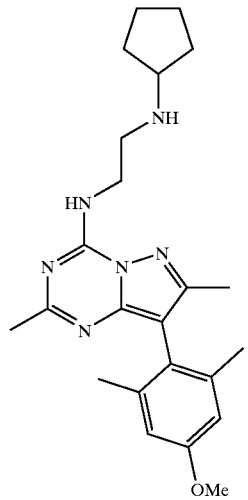

Dissolve 2,6-dimethyl-7-(2,6-dimethyl-4-methoxyphenyl)-4-(2-aminoethyl)amino-[1,5-a]-pyrazolo-1,3,5-triazine from step D (0.211 g) in dry dichloroethane (15 mL) and add cyclopentanone (1 equiv). Add acetic acid (35 µL) followed by sodium triacetoxyborohydride (0.184 g) and stir the resulting homogeneous mixture overnight at ambient temperature. Dilute the reaction mixture with 4 volumes of CH$_2$Cl$_2$, wash with brine, dry over anhydrous sodium sulfate, and concentrate under reduced pressure to obtain a yellow solid. Purify using preparative thin-layer chromatography [10% MeOH(2N NH$_3$)/CH$_2$Cl$_2$] to obtain 7-(2-(cyclopentylamino)ethylamino)-2,5-dimethyl-3-(4-methoxy-2,6-dimethylphenyl)-[1,5-a]-pyrazolo-1,3,5-triazine.

Example 6

Preparation of 7-(2-(cyclopentylamino)ethylamino)-2,5-dimethyl-3-(4-ethoxy-2,6-dichlorophenyl)-[1,5-a]-pyrazolo-1,3,5-triazine formula I where X is N, R$^1$ is CH$_3$, R$^2$ is H, A is CH$_2$, B is CH$_2$, R$^3$ is CH$_3$, R$^4$ is 2,6-dichloro-4-ethoxyphenyl, R$^5$ is cyclopentyl

A. (Iminoethyl)[4-(4-ethoxy-2,6-dichlorophenyl)-3-methylpyrazol-5-yl]amine acetate salt

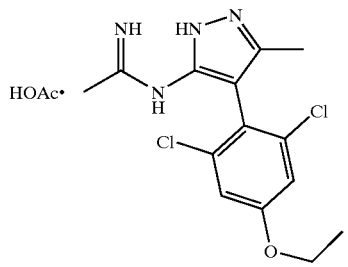

To a solution of 5-amino-4-(4-ethoxy-2,6-dichlorophenyl)-3-methylpyrazole (4.8 g) in acetonitrile (50 mL) add ethylacetimidate (free base, 2.3 mL) followed by acetic acid (0.96 mL). Collect the precipitate that formed upon stirring overnight by filtration. Wash the solid with dry ether and dry to afford 5.02 g of (iminoethyl)[4-(4-ethoxy-2,6-dichlorophenyl)-3-methylpyrazol-5-yl]amine acetate salt as a white powder.

B. 2,6-Dimethyl-7-(2,6-dichloro-4-ethoxyphenyl)-3H-[1,5-c]-pyrazolo-1,3,5-triazin-4-one

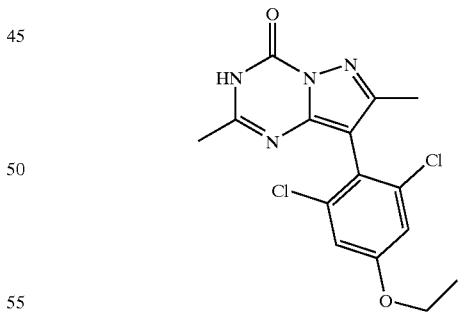

Add sodium pieces (2.98 g) to a flask containing anhydrous ethanol and equipped with a reflux condenser. Allow the mixture to stir until all the sodium is consumed and then add the amidine (5.02 g as the acetate salt) from step A in one portion. Add diethyl carbonate (12.6 mL) and reflux the mixture for four h. Concentrate the mixture under reduced pressure, dissolve the residue in water (75 mL) and adjust the pH to 5 with 3N HCl. Extract the aqueous mixture with EtOAc and wash the extracts with brine, dry over anhydrous sodium sulfate, and concentrate in vacuo to obtain a foam.

Stir the residue with hexanes for 20 min and collect the solid by filtration, then wash with hexanes to obtain 4.41 g of 2,6-dimethyl-7-(2,6-dichloro-4-ethoxyphenyl)-3H-[1,5-c]-pyrazolo-1,3,5-triazin-4-one as a beige solid: MS 353 (M+H).

C. 4-Chloro-2,6-dimethyl-7-(2,6-dichloro-4-ethoxyphenyl) [1,5-a]-pyrazolo-1,3,5-triazine

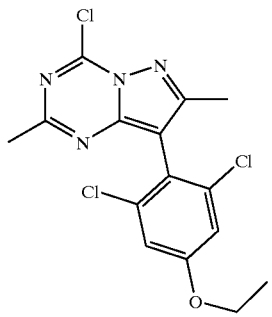

Dissolve 2,6-dimethyl-7-(2,6-dichloro-4-ethoxyphenyl)-3H-[1,5-c]-pyrazolo-1,3,5-triazin-4-one from step B (1.05 g) in POCl$_3$ (50 mL) and add 2,6-lutidine (0.45 mL). Reflux the reaction mixture under a dry nitrogen atmosphere for 48 h and then concentrate the mixture under reduced pressure. Dissolve the residue in EtOAc and wash with a saturated aqueous NaHCO$_3$ solution, then with brine. Dry the organic layer over anhydrous sodium sulfate, filter and concentrate under reduced pressure to obtain an oil which crystallizes upon standing. Wash the solid with hexanes to remove residual 2,6-lutidine and collect the solid on a sintered glass funnel yielding 4-chloro-2,6-dimethyl-7-(2,6-dichloro-4-ethoxyphenyl) [1,5-a]-pyrazolo-1,3,5-triazine. MS 372 (M+H).

D. 2,6-Dimethyl-7-(2,6-dichloro-4-ethoxyphenyl)-4-(2,2-dimethoxyethyl)amino-[1,5-a]-pyrazolo-1,3,5-triazine

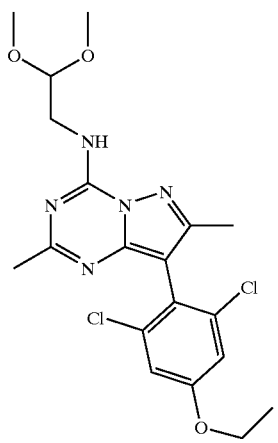

Dissolve the product from step C in dry acetonitrile and then add 2.1 equivalents of aminoacetaldehyde dimethyl acetal. Heat the solution to 60° C. and stir under a dry nitrogen atmosphere for 2–6 h. Remove the solvent under reduced pressure, dilute with 10% NaOH and extract with EtOAc. Wash the combined extracts with brine, dry over anhydrous sodium sulfate and concentrate under reduced pressure to obtain a yellow oil which crystallizes upon standing. The product, 2,6-dimethyl-7-(2,6-dichloro-4-ethoxyphenyl)-4-(2,2-dimethoxyethyl)amino-[1,5-a]-pyrazolo-1,3,5-triazine, is used without further purification. MS (M+H).

E. 2-{[7-(2,6-dichloro-4-ethoxyphenyl)-2,5,6-trimethyl-3-pyrazolino[2,3-a]1,3,5-triazin-4-yl]amino}ethanal

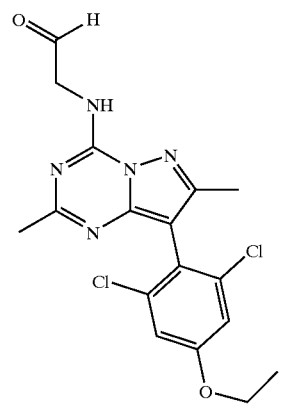

Dissolve the product obtained from step D in neat trifluoroacetic acid (25 mL). After allowing the mixture to stand at ambient temperature for 0.5 h, concentrate the mixture under reduced pressure. Add saturated aqueous sodium bicarbonate and stir the resulting heterogeneous mixture for 0.5 h. Extract the aqueous solution with EtOAc, wash the EtOAc extracts with brine and then dry over anhydrous sodium sulfate. Evaporation of the solvent under reduced pressure yields the aldehyde as an off-white foam. $^1$H NMR (CDCl13): δ 9.79 (s, 1H, CHO).

F. 7-(2(Cyclopentylamino)ethylamino)-2,5-dimethyl-3-(4-ethoxy-2,6-dichlorophenyl)-[1,5-a]-pyrazolo-1,3,5-triazine

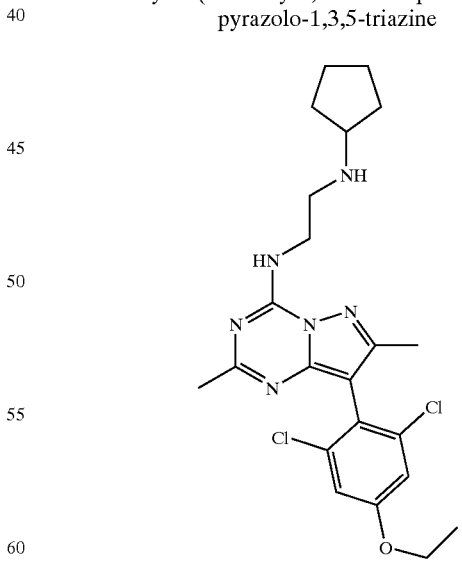

Dissolve the aldehyde (62 mg, 0.16 mmol) obtained from step E in dry dichloroethane (4 mL). Add 1.1 equivalents of cyclopentylamine followed by 1 equivalent of acetic acid. After the addition of sodium triacetoxyborohydride (1.4 eq), stir the solution at ambient temperature for several h. Dilute the reaction mixture with 4 volumes of $CH_2Cl_2$ then wash the mixture with brine (1x), dry over anhydrous Na2SO4. Concentrate under reduced pressure. Preparative thin layer chromatography [10% $MeOH(2N\ NH_3)/CH_2Cl_2)$] of the oily residue yields 7-(2-(cyclopentylamino)ethylamino)-2,5-dimethyl-3-(4-ethoxy-2,6-dichlorophenyl)-[1,5-a]-pyrazolo-1,3,5-triazine.

The preparation of the compounds of the present invention by the above-mentioned methods is illustrated further by the following examples, delineated in the TABLE which are not to be construed as limiting the invention in scope or spirit to the specific procedures and compounds described in them. Commonly used abbreviations are: Ph is phenyl, Me is methyl, Et is ethyl, Pr is n-propyl, iPr is isopropyl, cPr is cyclopropyl, Bu is butyl, iBu is isobutyl ($CH_2$—$CHMe_2$), tBu is tert-butyl, cBu is cyclobutyl, Pent is n-pentyl, cPent is cyclopentyl, cHex is cyclohexyl, Py is pyridyl, Bn is benzyl ($CH_2Ph$), Ac is acetyl ($CH_3$—(C=O)), tBOC is tert-butyloxycarbonyl (tBuO—(C=O)). EX means example.

By way of further exemplification, details of the preparation used in Example 14 which is included in the Table are as follows:

Example 14

Preparation of N-cyclopentyl-N'-[3-(2,3-dichlorophenyl)-2,5-dimethyl-pyrazolo[1,5-a]pyrimidin-7-yl]-ethane-1,2-diamine hydrochloride salt formula I where X is CH, $R^1$ is $CH_3$, $R^2$ is H, A is $CH_2$, B is $CH_2$, $R^3$ is $CH_3$, $R^4$ is 2,3-dichloro-4-ethoxyphenyl, $R^5$ is cyclopentyl, $R^6$ is H

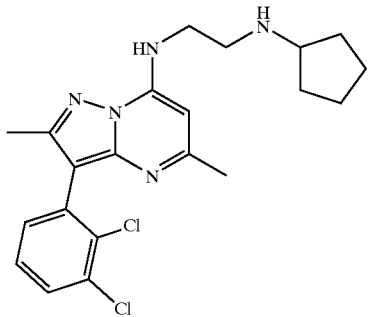

A. 7-Chloro-2,5-dimethyl-pyrazolo[1,5-a]pyrimidine 2,5-Dimethyl-4H-pyrazolo[1,5-a]pyrimidin-7-one (3.5 g, 21 mmol) in phosphorus oxychloride (20 mL) was stirred at reflux. After 3 hours the dark purple reaction was cooled and then extracted from ice water with ethyl acetate. The combined organic layers were washed with water and saturated aqueous sodium bicarbonate, dried ($Na_2SO_4$) and then concentrated under reduced pressure to give the title compound (3.0 g, 77%) as a brown solid: +APcI MS (M+1)$^+$ 182; H NMR (CDCl$_3$) δ: 6.74 (s, 1H), 6.42 (s, 1H), 2.55 (s, 3H), 2.53 (s, 3H).

B. N-(2,5-Dimethyl-pyrazolo[1,5-a]pyrimidin-7-yl)-ethane-1,2-diamine

To a stirred solution of 7-chloro-2,5-dimethyl-pyrazolo [1,5-a]pyrimidine (3.0 g, 16.5 mmol) in ethanol (60 mL) was added ethylene diamine (4 mL, 60 mmol). After refluxing 18 hours the reaction was cooled, poured into saturated aqueous sodium bicarbonate, and then washed with ethyl acetate. The aqueous layer was then extracted with 3:7 isopropyl alcohol/chloroform, the combined extracts were dried ($Na_2SO_4$) and then concentrated under reduced pressure to give the title compound as an amorphous brown solid (3.2 g, 94%): +APcI MS (M+1)$^+$ 206; $^1$H NMR (methanol-d$_4$) δ: 6.05 (s, 1H), 6.00 (s, 1H), 3.45 (m, 2H), 2.91 (m, 2H).

C. N-Cyclopentyl-N'-(2,5-dimethyl-pyrazolo[1,5-a]pyrimidin-7-yl)-ethane-1,2-diamine To a stirred solution of N-(2,5-dimethyl-pyrazolo[1,5-a] pyrimidin-7-yl)-ethane-1,2-diamine (3.2 g, 16 mmol) and cyclopentanone (2.7 mL, 30 mmol) in methanol (30 mL)/ acetic acid (3 mL) was added sodium cyanoborohydride (0.94 g, 15 mmol), portionwise. After stirring 1 hour the reaction was concentrated under reduced pressure and then extracted from saturated aqueous sodium bicarbonate with ethyl acetate. The combined extracts were dried ($Na_2SO_4$), concentrated under reduced pressure to give the crude product as a brown oil (5.6 g): +APcI MS (M+1)$^+$ 274; $^1$H NMR (CDCl$_3$) δ: 6.11 (s, 1H), 6.76 (s, 1H), 3.21 (t, 2H), 3.21 (m, 1H ), 3.04 (t, 1H), 2.42 (s, 3H), 2.40 (s, 3H).

D. Cyclopentyl-[2-(2,5-dimethyl-pyrazolo[1,5-a]pyrimidin-7-ylamino)-ethyl]-carbamic acid tert-butyl ester To a stirred solution of the crude N-cyclopentyl-N'-(2,5-dimethyl-pyrazolo[1,5-a]pyrimidin-7-yl)-ethane-1,2-diamine (5.6 g) in methylene chloride (24 mL)/methanol (2 mL) was added di-tert-butyl dicarbonate (5.1 g, 23 mmol) and then 4-dimethylaminopyridine (0.6 g, 4.9 mmol). After stirring 5 hours the reaction was concentrated under reduced pressure and then chromatographed (1:1 ethyl acetate/ hexanes) to afford the title compound as an orange glass (2.3 g 39% from B)): +APcI MS (M+1)$^+$ 374; $^1$H NMR (CDCl$_3$) δ: 6.16 (s, 1H), 5.78 (s, 1H), 4.25–4.15 (br s, 1H), 3.47 (m, 4H), 2.47 (s, 3H), 2.41 (s, 3H), 1.51 (s, 9H).

E. Cyclopentyl-[2-(3-iodo-2,5-dimethyl-pyrazolo[1,5-a]pyrimidin-7-ylamino)-ethyl]-carbamic acid tert-butyl ester To a 0° C. stirred solution of cyclopentyl-[2-(2,5-dimethyl-pyrazolo[1,5-a]pyrimidin-7-ylamino)-ethyl]-carbamic acid tert-butyl ester (89 mg, 0.24 mmol) in chloroform (5 mL) was added N-iodosuccinimide (54 mg, 0.24 mmol). After stirring 30 minutes the reaction was extracted from saturated aqueous sodium thiosulfate with chloroform. The combined extracts were dried ($Na_2SO_4$), concentrated under reduced pressure to give the product as a slightly yellowed glass (102 mg, 85%): +APcI MS (M+1)$^+$ 500; $^1$H NMR (CDCl$_3$) δ: 5.82 (s, 1H), 4.25–4.10 (br s, 1H), 3.46 (s, 4H), 2.51 (s, 3H), 2.41 (s, 3H), 1.50 (s, 9H).

F. Cyclopentyl-{2-[3-(2,3-dichloro-phenyl)-2,5-dimethyl-pyrazolo[1,5-a]pyrimidin-7-ylamino]-ethyl}-carbamic acid tert-butyl ester A suspension of cyclopentyl-[2-(3-iodo-2,5-dimethyl-pyrazolo[1,5-a]pyrimidin-7-ylamino)-ethyl]-carbamic acid tert-butyl ester (38 mg, 0.076 mmol) and 2,3-dichlorobenzeneboronic acid in toluene (0.5 mL)/ethanol (0.5 mL)/2 M aqueous sodium carbonate (0.22 mL) was degassed (3x) by alternately pulling a vacuum followed by repressurization with nitrogen. Tetrakis(triphenylphosphine) palladium (10 mg, 0.009 mmol) was added, and the mixture was degassed (3x) again. The mixture was stirred for 2.5 hours at 100° C., concentrated under reduced pressure, and then chromatographed (4:1 hexanes/ethyl acetate) to give the product as colorless oil (24 mg, 60%): +APcI MS (M+1)+ 518; $^1$H NMR (CDCl$_3$) δ7.42 (dd, 1 H), 7.30 (dd, 1H), 7.22 (t, 1H), 5.84 (s, 1H ), 4.25–4.10 (br s, 1H), 3.49 (s, 4H), 2.44 (s, 3H), 2.32 (s, 3H), 1.52 (s, 9H).

G. N-Cyclopentyl-N'-[3-(2,3-dichloro-phenyl)-2,5-dimethyl-pyrazolo[1,5-a]pyrimidin-7-yl]-ethane-1,2-diamine hydrochloride salt The cyclopentyl-{2-[3-(2,3-dichloro-phenyl)-2,5-dimethyl-pyrazolo[1,5-a]pyrimidin-7-ylamino]-ethyl}-carbamic acid tert-butyl ester (21 mg, 0.040 mmol) was stirred for 1 hour in 2:1 ethanol/concentrated aqueous hydrochloric acid (1.5 mL), concentrated under reduced pressure, and then concentrated 2 additional times from ethanol to give the title compound (17 mg, 94%): +APcI MS (M+1)+ 418; $^1$H NMR (methanol-d$_4$) δ: 7.69 (d, 1H), 7.50–7.40 (m, 2H), 6.78 (s, 1H), 4.06 (br s, 2H), 3.63 (br m, 1H), 3.42 (br s, 2H), 2.60 (s, 3H), 2.34 (s, 3H).

Table of Examples

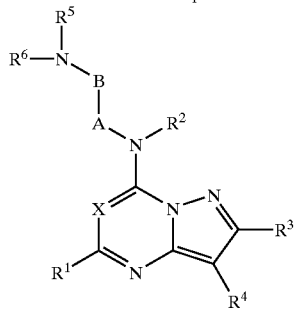

| EX | X | R$^1$ | R$^2$ | R$^3$ | R$^4$ | A-B-N[R$^6$]-R$^5$ | MW |
|---|---|---|---|---|---|---|---|
| 7. | CH | Me | H | Me | 2-Cl-4-F—Ph | (CH2)2—NH-cHex | 415.93 |
| 8. | CH | Me | H | Me | 2-Cl-4-F—Ph | (CH2)2—NH-cPent | 401.92 |
| 9. | CH | Me | H | Me | 2-Cl-4-OEt—Ph | (CH2)2—NH-cPent | 427.98 |
| 10. | CH | Me | H | Me | 2-Cl-6-F—Ph | (CH2)2—NH-cPent | 401.91 |
| 11. | CH | Me | H | Me | 2-Cl—Ph | (CH2)2—NH-cPent | 383.93 |
| 12. | CH | Me | H | Me | 2-F-4-Br—Ph | (CH2)2—NH-cPent | 482.83 |
| 13. | CH | Me | H | Me | 2-F—Ph | (CH2)2—NH-cPent | 367.47 |
| 14. | CH | Me | H | Me | 2,3-diCl—Ph | (CH2)2—NH-cPent | 418.37 |
| 15. | CH | Me | H | Me | 2,4-diCl-6-OMe—Ph | (CH2)2—NH-cPent | 448.4 |
| 16. | CH | Me | H | Me | 2,4-diCl—Ph | (CH2)2—NH-cBu | 404.24 |
| 17. | CH | Me | H | Me | 2,4-diCl—Ph | (CH2)2—NH—CH2-cPr | 404.34 |
| 18. | CH | Me | H | Me | 2,4-diCl—Ph | (CH2)2—NH-cHex | 432.39 |
| 19. | N | Me | H | Me | 2,4-diCl—Ph | (CH2)2—NH-cHex | 433.4 |
| 20. | CH | Me | H | Me | 2,4-diCl—Ph | (CH2)2—NH-cPent | 418.36 |
| 21. | N | Me | H | Me | 2,4-diCl—Ph | (CH2)2—NH-cPent | 419.4 |
| 22. | CH | Me | H | Me | 2,4-diF-6-OEt—Ph | (CH2)2—NH-cPent | 465.98 |
| 23. | CH | Me | H | Me | 2,4-diF—Ph | (CH2)2—NH-cHex | 399.48 |
| 24. | CH | Me | H | Me | 2,4-diF—Ph | (CH2)2—NH-cPent | 385.45 |
| 25. | CH | Me | H | Me | 2,4-diOMe-6-Cl—Ph | (CH2)2—NH-cPent | 443.98 |
| 26. | CH | Me | H | Me | 2,4-diOMe-6-Cl—Ph | (CH2)2—NH2 | 375.9 |
| 27. | CH | Me | H | Me | 2,4-diOMe—Ph | (CH2)2—NH-cHex | 423.55 |
| 28. | CH | Me | H | Me | 2,4,6-triF—Ph | (CH2)2—NH-cPent | 439.91 |
| 29. | CH | Me | H | Me | 2,4,6-triMe—Ph | CH2-(2-Me-piperidin-6-yl) | 391.6 |
| 30. | CH | Me | H | Me | 2,4,6-triMe—Ph | (CH2)2—NH-cBu | 377.53 |
| 31. | CH | Me | H | Me | 2,4,6-triMe—Ph | (CH2)2—NH—CH2-cPr | 377.53 |
| 32. | CH | Me | H | Me | 2,4,6-triMe—Ph | (CH2)2—NH-cHex | 405.59 |
| 33. | CH | Et | H | Me | 2,4,6-triMe—Ph | (CH2)2—NH-cHex | 419.61 |
| 34. | CH | Me | H | Me | 2,4,6-triMe—Ph | (CH2)2—NH-cPent | 391.55 |
| 35. | CH | Me | H | CF3 | 2,4,6-triMe—Ph | (CH2)2—NH-cPent | 445.52 |
| 36. | N | Me | H | Me | 2,4,6-triMe—Ph | (CH2)2—NH-cPent | 392.5 |
| 37. | CH | Et | H | Me | 2,4,6-triMe—Ph | (CH2)2—NH-cPent | 405.59 |
| 38. | CH | Me | H | Me | 2,4,6-triMe—Ph | (CH2)2—NH-iBu | 379.55 |
| 39. | CH | Me | H | Me | 2,4,6-triMe—Ph | (CH2)2—NH-iPr | 365.52 |
| 40. | CH | Me | H | Me | 2,4,6-triMe—Ph | (CH2)2—NH-tBu | 379.54 |
| 41. | CH | Me | H | Me | 2,4,6-triMe—Ph | (CH2)2—NH-cPent | 405.59 |
| 42. | CH | Me | H | Me | 2,5-diCl—Ph | (CH2)2—NH-cPent | 418.37 |
| 43. | CH | Me | H | Me | 2,5-diF—Ph | (CH2)2—NH-cHex | 385.46 |
| 44. | N | Me | H | Me | 2,5-diMe-4-OMe—Ph | (CH2)2—NH-cHex | 422.6 |
| 45. | CH | Me | H | Me | 2,5-diMe-4-OMe—Ph | (CH2)2—NH-cHex | 421.59 |
| 46. | N | Me | H | Me | 2,5-diMe-4-OMe—Ph | (CH2)2—NH-cPent | 408.5 |
| 47. | CH | Me | H | Me | 2,6-diCl-4-OEt—Ph | (CH2)2—NH—(CH2)2—NH2 | 394.31 |
| 48. | CH | Me | H | Me | 2,6-diCl-4-OEt—Ph | (CH2)2—NH—CH2—CMe2—NH2 | 422.36 |
| 49. | N | Me | H | Me | 2,6-diCl-4-OEt—Ph | (CH2)2—NH2 | 395.3 |
| 50. | CH | Me | H | Me | 2,6-diCl-4-OEt—Ph | CH2—CHMe—NH2 | 408.33 |

Table of Examples

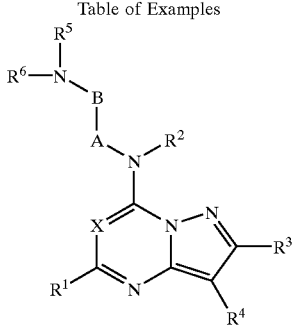

| EX | X | R¹ | R² | R³ | R⁴ | A-B-N[R⁶]-R⁵ | MW |
|---|---|---|---|---|---|---|---|
| 51. | CH | Me | H | Me | 2,6-diCl-4-OH—Ph | (CH2)2—NH-cPent | 434.37 |
| 52. | CH | Me | H | Me | 2,6-diCl-4-OMe—Ph | 4-NH2-cHex | 434.37 |
| 53. | CH | Me | H | Me | 2,6-diCl-4-OMe—Ph | 4-NH2-cHex | 434.37 |
| 54. | CH | iPr | H | Me | 2,6-diCl-4-OMe—Ph | (CH2)2—CHEt—NH2 | 450.4 |
| 55. | CH | Me | H | Me | 2,6-diCl-4-OMe—Ph | CH2-(2-Me-piperidin-6-yl) | 448.4 |
| 56. | CH | Me | H | Me | 2,6-diCl-4-OMe—Ph | (CH2)2—N(CH2-cPr)2 | 488.46 |
| 57. | CH | Me | H | Me | 2,6-diCl-4-OMe—Ph | (CH2)2—NH-(3-NH2-cHex) | 434.37 |
| 58. | CH | Me | H | Me | 2,6-diCl-4-OMe—Ph | (CH2)2—NH-(cis-2-NH2-cHex) | 434.37 |
| 59. | CH | Me | H | Me | 2,6-diCl-4-OMe—Ph | (CH2)2—NH-(trans-2-NH2-cHex) | 434.37 |
| 60. | CH | Me | H | Me | 2,6-diCl-4-OMe—Ph | (CH2)2—NH—CH2-cPr | 434.37 |
| 61. | CH | Me | H | Me | 2,6-diCl-4-OMe—Ph | (CH2)2—NH—CHMe—Et | 436.39 |
| 62. | CH | Me | H | Me | 2,6-diCl-4-OMe—Ph | (CH2)2—NH-cPent | 448.4 |
| 63. | CH | Me | H | Me | 2,6-diCl-4-OMe—Ph | (CH2)2—NH—Et | 408.33 |
| 64. | CH | Me | H | Me | 2,6-diCl-4-OMe—Ph | (CH2)2—NH2 | 380.28 |
| 65. | CH | iPr | H | Me | 2,6-diCl-4-OMe—Ph | (CH2)2—NH2 | 408.33 |
| 66. | CH | tBu | H | Me | 2,6-diCl-4-OMe—Ph | (CH2)2—NH2 | 422.4 |
| 67. | CH | nPr | H | Me | 2,6-diCl-4-OMe—Ph | (CH2)2—NH2 | 408.3 |
| 68. | CH | CF3 | H | Me | 2,6-diCl-4-OMe—Ph | (CH2)2—NH2 | 434.3 |
| 69. | CH | Me | H | Me | 2,6-diCl-4-OMe—Ph | (CH2)3—NH—Et | 422.36 |
| 70. | CH | Me | H | Me | 2,6-diCl-4-OMe—Ph | (CH2)3—NH2 | 394.31 |
| 71. | CH | Me | H | Me | 2,6-diCl-4-OMe—Ph | CH2-(piperidin-2-yl) | 434.3 |
| 72. | CH | Me | H | Me | 2,6-diCl-4-OMe—Ph | CH2—CHMe—NH2 | 394.3 |
| 73. | CH | Et | H | Me | 2,6-diCl-4-OMe—Ph | CH2—CHMe—NH2 | 408.33 |
| 74. | CH | iPr | H | Me | 2,6-diCl-4-OMe—Ph | CH2—CHMe—NH2 | 422.36 |
| 75. | CH | nPr | H | Me | 2,6-diCl-4-OMe—Ph | CH2—CHMe—NH2 | 422.36 |
| 76. | CH | Me | H | Me | 2,6-diCl-4-OMe—Ph | CH2—CMe2—CH2—NH2 | 422.36 |
| 77. | CH | Me | H | Me | 2,6-diCl-4-OMe—Ph | CH2—CMe2—CH2—NH2 | 477.44 |
| 78. | CH | Me | H | Me | 2,6-diCl-4-OMe—Ph | CH2—CMe2—NH2 | 408.33 |
| 79. | CH | Me | H | Me | 2,6-diCl-4-OMe—Ph | CHMe—CHMe—NH2 | 408.33 |
| 80. | CH | Et | H | Me | 2,6-diCl-4-OMe—Ph | CHMe—CHMe—NH2 | 422.4 |
| 81. | CH | Me | H | Me | 2,6-diCl-4-OMe—Ph | pyrrolidin-3-yl | 406.3 |
| 82. | CH | Me | H | Me | 2,6-diCl—Ph | (CH2)2—NH-cPent | 418.37 |
| 83. | N | Me | H | Me | 2,6-diCl—Ph | (CH2)2—NH-cPent | 419.4 |
| 84. | CH | Me | H | Me | 2,6-diCl—Ph | (CH2)2—NH—Et | 378.30 |
| 85. | CH | Me | H | Me | 2,6-diF-4-OEt—Ph | (CH2)2—NH-cPent | 465.98 |
| 86. | CH | Me | H | Me | 2,6-diF—Ph | (CH2)2—NH-cPent | 385.46 |
| 87. | CH | Me | H | Me | 2,6-diMe-4-OCF3—Ph | (CH2)2—NH-cPent | 461.52 |
| 88. | N | Me | H | Me | 2,6-diMe-4-OMe—Ph | (CH2)2—NH2 | 340.4 |
| 89. | CH | Me | H | Me | 2,6-diMe-4-tBu—Ph | (CH2)2—NH-cPent | 433.65 |
| 90. | N | Me | H | Me | 2Cl-4F—Ph | (CH2)2—NH-cHex | 416.9 |
| 91. | N | Me | H | Me | 2Cl-4F—Ph | (CH2)2—NH-cPent | 402.9 |

Example 92

Cyclopentyl-{1-[3-(2,6-dichloro-4-methoxy-phenyl)-2,5-dimethyl-pyrazolo[1,5-a]pyrimidin-7-yl]-piperidin-3-yl}-amine (MW 488.5)

Example 93

7-piperazino-2,5-dimethyl-3-(2,4-dichlorophenyl)-pyrazolo[1,5-a] pyrimidine (MW 376.28)

Example 94

Characterization of NPY receptor interactions and in vivo function

A. Assay for Human $NPY_1$ Receptor Binding Activity: Compounds are assayed for activity using the following method: A cDNA encoding human NPY1 (SEQ ID NO:1) is ligated in the appropriate orientation for expression into the commercial expression vector pBacPAK9 (Clontech, Palo Alto, Calif.) for expression in SF9 cells. Each Baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing 2×10⁶ Sf9 cells in 5 mls of insect medium. After five days of incubation at 27° C., supernatant medium is harvested from each of the T25 infections for use as passage 1 inoculum. Recombinant baculoviral clones are then subjected to a second round of amplification, using 1 ml of passage 1 stock to infect 1×10⁸ cells in 100 ml of insect medium divided into 2 T175 flasks. Forty-eight hours post infection, passage 2 medium is harvested from each 100 ml prep and plaque assayed for titer. The cell pellets from the second round of amplification are assayed for affinity binding of radiolabeled ligand (see below) to verify recombinant receptor expression. A third round of amplification is then initiated using an M.O.I. of 0.1 to infect a liter of Sf9 cells. Forty hours post-infection the supernatant medium is harvested to yield passage 3 baculoviral stock and the cell pellet assayed for affinity binding. Titer of the passage 3 baculoviral stock is determined by plaque assay and an M.O.I. and Incubation Time Course experiment is carried out to determine conditions for optimal receptor expression.

Log-phase Sf9 cells are infected with stocks of recombinant baculovirus encoding the proteins of interest (e.g., human NPY1 and three g-proteins), followed by culturing in insect medium at 27° C. 72 hours post-infection, a sample of cell suspension is analyzed for viability by trypan blue dye exclusion, and the remaining Sf9 cells are harvested via centrifugation (3000 rpm/10 min/ 4° C).

Preparation of purified membranes: Sf9 cell pellets are resuspended in homogenization buffer (10 mM HEPES, 250 mM sucrose, 0.5 □g/ml leupeptin, 2 □g/ml Aprotinin, 200 □M PMSF, and 2.5 mM EDTA, pH 7.4) and homogenized using a POLYTRON homogenizer (setting 5 for 30 seconds). The homogenate is centrifuged (536×g/10 min/4° C.) to pellet the nuclei. The supernatant containing isolated membranes is decanted to a clean centrifuge tube, centrifuged (48,000×g/30 min, 4° C.) and resuspended in 30 ml, or preferably 20 ml of homogenization buffer. This centrifugation and resuspension step is repeated twice. The final pellet is resuspended in ice cold Dulbecco's PBS containing 5 mM EDTA and stored in frozen aliquots until needed at −80° C. The protein concentration of the resulting membrane preparation is measured using the Bradford protein assay (Bio-Rad Laboratories, Hercules, Calif.). By this measure, a 1-liter culture of cells typically yields 50–100 mg of total membrane protein.

CO-infection for GTP$\gamma^{35}$S binding assay: Four baculoviral expression vector stocks are used to infect a culture of Sf9 cells with an MOI of 1:1:1:1. These four consisted of one vector encoding the human NPY1 receptor and a different commercially obtained baculoviral expression vector stock encoding each of the three subunits of a heterotrimeric G-protein, in particular, the G-protein-encoding virus stocks are obtained from BIOSIGNAL Inc., Montreal, and are 1) a Gα G-protein subunit-encoding virus stock (either the rat Gα$_{i2}$ G-protein-encoding virus stock BIOSIGNAL #V5J008 or the rat Gα$_o$ G-protein-encoding virus stock BIOSIGNAL #V5H010), 2) a bovine β1 G-protein-encoding virus stock (BIOSIGNAL #V5H012), and 3) a human γ2 G-protein-encoding virus stock (BIOSIGNAL #V6B003). Agonist-stimulated GTP$\gamma^{35}$S binding on purified membranes is assessed using hNPY 1–36 (American Peptide Co., Sunnyvale, Calif.) as agonist in order to ascertain functional activity as measured by GTP$\gamma^{35}$S binding.

B. GTP$\gamma^{35}$S binding assay: Purified Sf9 cell membranes are resuspended by Dounce homogenization (tight pestle) in GTP$\gamma^{35}$S binding assay buffer (50 mM Tris pH 7.0, 120 mM NaCl, 2 mM MgCl2, 2 mM EGTA, 0.1% BSA, 0.1 mM bacitracin, 100KIU/mL Aprotinin, 5 μM GDP) and added to reaction tubes at a concentration of 30 μg/reaction tube. After adding increasing doses of the agonist hNPY 1–36 (American Peptide Co., Sunnyvale, Calif.), reactions are initiated by the addition of 100 pM GTP$\gamma^{35}$S. Following a 30-minute incubation at ambient temperature, the reactions are terminated by vacuum filtration over GF/C filters (presoaked in wash buffer, 0.1% BSA) followed by washing with ice-cold wash buffer (50 mM Tris pH 7.0, 120 mM NaCl). Bound GTP$\gamma^{35}$S is determined by liquid scintillation spectrometry of the washed filters. Non-specific binding is determined using 10 mM GTPγS. Data are generally expressed as % maximal response and are derived by determining the maximal agonist stimulated % above basal stimulation. Computer analysis may be conveniently used to calculate estimated $EC_{50}$, $IC_{50}$ and $K_i$ values from GTP$\gamma^{35}$S binding experiment data, e.g., using SigmaPlot software. The binding affinity for the preferred compounds of the invention, expressed as $K_i$ values, ranges from about 0.1 nanomolar to about 5 micromolar. Particularly preferred compounds yield a $K_i$ value of less than 100 nanomolar, most preferably less than 10 nanomolar.

Assay for affinity binding of radiolabeled ligand: Purified membranes are washed with PBS and re-suspended by gentle pipetting in binding buffer (50 mM Tris(HCl), 5 mM KCl, 120 mM NaCl, 2 mM CaCl2, 1 mM MgCl2, 0.1% bovine serum albumin (BSA), pH 7.4). Membranes (5 μg) are added to siliconized (Sigmacote, Sigma) polypropylene tubes in addition to 0.050 nM [125I]NPY (porcine, New England Nuclear Corp., Boston, Mass.) for competition analysis or 0.010–0.500 nM [125I]NPY (porcine) for saturation analysis. For evaluation of guanine nucleotide effects on receptor affinity, GTP is added at a final concentration of 100 μM. Cold displacers are added at concentrations ranging from 10–12 M to 10–6 M to yield a final volume of 0.250 mL. Nonspecific binding is determined in the presence of 1 μM NPY (human, American Peptide Co., Sunnyvale, Calif.) and accounts for less than 10% of total binding. Following a 2-hour incubation at ambient temperature, the reaction is terminated by rapid vacuum filtration. Samples are filtered over presoaked GF/C Whatman filters (1.0% polyethyleneimine for 2 hours) and rinsed 2 times with 5 mL cold binding buffer lacking BSA. Remaining bound radioactivity is measured by gamma counting. To estimate the Bmax, Kd and Ki, the results of binding experiments are analyzed using SigmaPlot software (SPSS Science, Chicago, Ill.). The binding.affinity for the compounds of the invention, expressed as a Ki value, ranges from about 0.1 nanomolar to about 10 micromolar. The most preferred compounds of the invention have a Ki of less than 100 nanomolar and a binding selectivity of >100-fold relative to other G-protein coupled receptors, including NPY$_5$ and CRF1$_1$ receptors.

C. In vivo Analysis—Food Deprivation

Subjects. Experimentally naive and experienced male Sprague-Dawley rats (Sasco, St. Louis, Mo.) weighing 210–300 g at the beginning of the experiment are used. Animals are triple-housed in stainless steel hanging cages in a temperature (22 C.±2) and humidity (40–70% RH) controlled animal facility with a 12:12 hour light-dark cycle. Food (Standard Rat Chow, PMI Feeds Inc., #5012) and water are available ad libitum.

Apparatus. Consumption data is collected while the animals are housed in Nalgene Metabolic cages (Model #650-0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment. The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, and body weight may be measured with an Ohaus Portable Advanced scale (±0.1 g accuracy).

Procedure. Prior to the day of testing, animals are habituated to the testing apparatus by placing each animal in a Metabolic cage for 1 hour. On the day of the experiment, animals that have been food deprived the previous night are weighed and assigned to treatment groups. Assignments are made using a quasi-random method utilizing the body weights to assure that the treatment groups had similar average body weight. Animals are then administered either vehicle (0.5% methyl cellulose) or drug (a compound of the invention). At that time, the feeding drawer is filled with pulverized chow, the filled water bottle, and the empty urine and feces collection tubes are weighed. Two hours after drug treatment, each animal is weighed and placed in a Metabolic Cage. Following a one-hour test session, animals are removed and body weight obtained. The food and water containers are then weighed and the food and water consumption data recorded.

Drugs. Drug suspended in vehicle, or vehicle alone as a control, is administered orally (PO) using a gavage tube connected to a 3 or 5 ml syringe at a volume of 10 ml/kg. Drug is made into a homogenous suspension by stirring and ultrasonicating for at least 1 hour prior to dosing.

Statistical Analyses. The means and standard errors of the mean (SEM) for food consumption, water consumption, and body weight change are obtained. One-way analysis of variance using Systat (5.2.1) is used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the 1-hour test session. Water consumption is the difference in the weight of the water bottle prior to testing and the weight following the 1-hour test session. Preferred compounds of the invention reduce food intake and body weight gain, preferably to a statistically significant degree as determined by standard parametric analysis such as a student's T-test.

Example 95
Assay for CRF Receptor Binding Activity

As discussed above, the following assay is defined herein as a standard in vitro CRF receptor binding assay. The assay may be used to demonstrate CRF1 receptor-binding activity. The CRF receptor binding is performed using a modified version of the assay described by Grigoriadis and De Souza (*Methods in Neurosciences,* Vol. 5, 1991). IMR-32 human neuroblastoma cells, a cell-line that naturally expresses the CRF1 receptor, are grown to confluency in DMEM containing FBS.

To prepare receptor-containing membranes, cells are homogenized in wash buffer (50 mM Tris HCl, 10 mM $MgCl_2$, 2 mM EGTA, pH 7.4) and centrifuged at 48,000 g for 10 min at 4° C. The pellet is re-suspended in wash buffer and the homogenization and centrifugation steps are performed two additional times.

Membrane pellets containing CRF receptors are re-suspended in 50 mM Tris buffer pH 7.7 containing 10 mM $MgCl_2$ and 2 mM EDTA and centrifuged for 10 min at 48000×g. Membranes are washed again and brought to a final concentration of 1500 mg/ml in binding buffer (Tris buffer above with 0.1% BSA, 15 mM bacitracin and 0.01 mg/ml aprotinin.). For the binding assay, 100 ml of the membrane preparation are added to 96 well microtube plates containing 100 ml of $^{125}$I-CRF (SA 2200 Ci/mmol, final concentration of 100 pM) and 50 ml of test compound. Binding is carried out at ambient temperature for 2 h. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass.). The binding affinity for a compound of Formula I expressed as an $IC_{50}$ value generally ranges from about 0.5 nanomolar to about 10 micromolar.

Example 96
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.;

Example 97
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 98

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

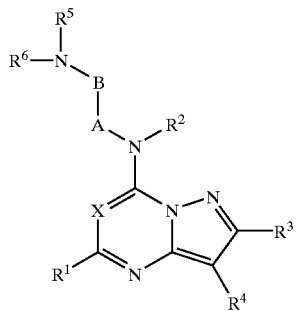

or a pharmaceutically acceptable salt or an acylated derivative wherein a free hydroxyl or amino group has been acylated to form a compound capable of acting as a prodrug thereof, wherein the compound exhibits a $K_i$ of 5 micromolar or less in a NPY1 receptor binding assay as determined by displacement of radiolabeled [125 I] NPY1 from the NPY receptor coded for by SEQ ID NO: 1 in which said radiolabeled [125 I] NPY was bound to, and X is $CR^{14}$;

$R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^2$ is
H,
$C_1$–$C_6$ alkyl which optionally forms a $C_3$–$C_6$ aminocarbocycle or a $C_2$–$C_5$ aminoheterocycle with A or B, each of which is optionally substituted with $R^7$,
$C_3$–$C_{10}$ cycloalkyl, or
($C_3$–$C_{10}$ cycloalkyl) $C_1$–$C_6$ alkyl; or $R^2$ and $R^6$ jointly form with the 2 nitrogen atoms to which they are bound a $C_2$–$C_5$ aminoheterocycle optionally substituted with $R^7$;

A is $(CH_2)_m$ where m is 1,2 or 3 and is optionally mono- or di-substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or
A and B jointly form a $C_3$–$C_6$ carbocycle, which is optionally substituted at each carbon atom with $R^7$, or
A and $R^2$ jointly form a $C_3$–$C_6$ aminocarbocycle, which is optionally substituted at each carbon atom with $R^7$;

B is $(CH_2)_n$ where n is 0, 1, 2, or 3 and is optionally substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or B and $R^2$ jointly form a $C_3$–$C_6$ aminocarbocycle, which is optionally substituted at each carbon atom with $R^7$, or B and $R^6$ jointly form a $C_3$–$C_6$ aminocarbocycle, which is optionally substituted at each carbon atom with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C^1$–$C_6$ alkyl-CN, $S_2NR^8R^9$, $SO_2R^7$, aryl, heteroaryl, heterocycloalkyl, and 3-, 4-, or 5-(2-oxo-1,3-oxazolidinyl), with the proviso that at least one of the positions ortho or para to the point of attachment of the aryl or heteroaryl ring to the pyrazole is substituted;

$R^5$ and $R^6$ are independently selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, and $C_2$–$C_6$ alkynyl, $R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each of which is optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that for $SO_2R^7$, $R^7$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $R^7$;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that for $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN.

2. A compound according to claim 1, wherein X is CH.

3. A compound according to claim 1, wherein
X is CH; and
$R^1$ is H, $C_1$–$C_6$ alkyl, $C_3$–$C_{10}$ cycloalkyl, or ($C_3$–$C_{10}$ cycloalkyl) $C_1$–$C_6$ alkyl.

4. A compound according to claim 1, wherein
X is CH;
$R^1$ is H, $C_1$–$C_6$ alkyl;
$R^2$ is H or $C_1$–$C_6$ alkyl; and
$R^3$ is $C_1$–$C_6$ alkyl, trifluoromethyl, or $C_1$–$C_6$alkyl-O $C_1$–$C_6$alkyl.

5. A compound according to claim 1 wherein the compound exhibits a 20-fold greater affinity for the NPY1 receptor in the NPY1 receptor binding assay than for the CRF1 receptor in an assay of CRF1 receptor as determined by binding to a radiolabeled ligand.

6. A compound according to claim 1 wherein the compound exhibits a 100-fold greater affinity for the NPY1 receptor in the NPY1 receptor binding assay than for the CRF1 receptor in an assay of CRF1 receptor as determined by binding to a radiolabeled ligand.

7. A method for treating eating disorders comprising administering to a patient suffering from an eating disorder a compound according to claim 1.

8. A method for treating obesity or bulimia nervosa which comprises administering an effective amount of a compound according to claim 1 to a patient in need thereof.

9. A compound of the formula

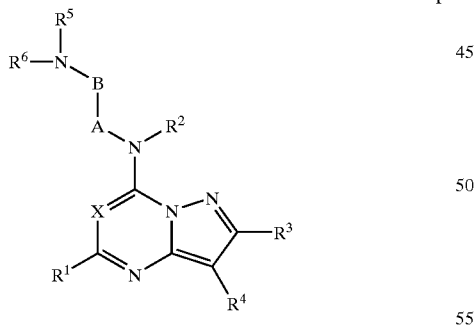

I or a pharmaceutically acceptable salt or an acylated derivative wherein a free hydroxyl or amino group has been acylated to form a compound capable of acting as a prodrug thereof, wherein the compound exhibits a $K_i$ of 5 micromolar or less in a NPY1 receptor binding assay as determined by displacement of radiolabeled [125 I] NPY from the NPY1 receptor coded for by SEQ ID NO.: 1 in which said radiolabeled [125 I] NPY was bound to, and X is $CR^{14}$;
$R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^2$ is
H,
$C_1$–$C_6$ alkyl which optionally forms a $C_3$–$C_6$ aminocarbocycle or a $C_2$–$C_5$ aminoheterocycle with A or B, each of which is optionally substituted with $R^7$,
$C_3$–$C_{10}$ cycloalkyl, or
($C_3$–$C_{10}$ cycloalkyl) $C_1$–$C_6$ alkyl; or $R^2$ and $R^6$ jointly form with the 2 nitrogen atoms to which they are bound a $C_2$–$C_5$ aminoheterocycle optionally substituted with $R^7$;

A is $(CH_2)_m$ where m is 1,2 or 3 and is optionally mono- or di-substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or A and B jointly form a $C_3$–$C_6$ carbocycle, which is optionally substituted at each carbon atom with $R^7$, or A and $R^2$ jointly form a $C_3$–$C_6$ aminocarbocycle, which is optionally substituted at each carbon atom with $R^7$;

B is $(CH_2)_n$ where n is 0, 1, 2, or 3 and is optionally substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8$, $R^9$, or $C_1$ $C_6$ alkyl-$NR^8R^9$, or B and $R^2$ jointly form a $C_3$–$C_6$ aminocarbocycle, which is optionally substituted at each carbon atom with $R^7$, or B and $R^6$ jointly form a $C_3$–$C_6$ aminocarbocycle, which is optionally substituted at each carbon atom with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C^1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, and 3-, 4-, or 5-(2-oxo-1,3-oxazolidinyl), with the proviso that at least one of the positions ortho or para to the point of attachment of the aryl or heteroaryl ring to the pyrazole is substituted;

$R^5$ is H;

$R^6$ and $C_3$–$C_{10}$ cycloalkyl, ($C_3$–$C_{10}$ cycloalkyl) $C_1$–$C_6$ alkyl;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each of which is optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that for $SO_2R^7$, $R^7$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $R^7$;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that for $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN.

10. A compound of the formula

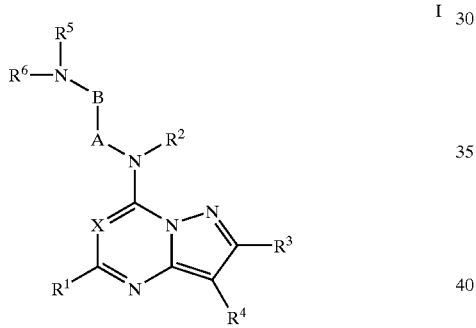

or a pharmaceutically acceptable salt or an acylated derivative wherein a free hydroxyl or amino group has been acylated to form a compound capable of acting as a prodrug thereof, wherein the compound exhibits a $K_i$ of 5 micromolar or less in a NPY1 receptor binding assay as determined by displacement of radiolabeled [125 I] NPY from the NPY1 receptor coded for by SEQ ID NO.: 1 in which said radiolabeled [125 I] NPY was bound to, and X is $CR^{14}$;

$R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^2$ is
H,
$C_1$–$C_6$ alkyl which optionally forms a $C_3$–$C_6$ aminocarbocycle or a $C_2$–$C_5$ aminoheterocycle with A or B, each of which is optionally substituted with $R^7$,
$C_3$–$C_{10}$ cycloalkyl, or
($C_3$–$C_{10}$ cycloalkyl) $C_1$–$C_6$ alkyl; or
$R^2$ and $R^6$ jointly form with the 2 nitrogen atoms to which they are bound a $C_2$–$C_5$ aminoheterocycle optionally substituted with $R^7$;

A is $(CH_2)_m$ where m is 1,2 or 3 and is optionally mono- or di-substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or A and B jointly form a $C_3$–$C_6$ carbocycle, which is optionally substituted at each carbon atom with $R^7$, or A and $R^2$ jointly form a $C_3$–$C_6$ aminocarbocycle, which is optionally substituted at each carbon atom with $R^7$;

B is $(CH_2)_n$ where n is 0, 1, 2, or 3 and is optionally substituted at each carbon atom with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halogen, $C_1$–$C_6$ haloalkyl, $OR^7$, $C_1$–$C_6$ alkyl-$OR^7$; $C_1$–$C_6$ cyanoalkyl, $NR^8R^9$, or $C_1$–$C_6$ alkyl-$NR^8R^9$, or B and $R^2$ jointly form a $C_3$–$C_6$ aminocarbocycle, which is optionally substituted at each carbon atom with $R^7$, or B and $R^6$ jointly form a $C_3$–$C_6$ aminocarbocycle, which is optionally substituted at each carbon atom with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, and $C_1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, halogen, $C_1$–$C_6$ haloalkyl, CN, alkylsulfonyl, $OR^7$, $NR^8R^9$, $CONR^8R^9$, $COOR^7$, $SO_2NR^8R^9$, $COR^7$, $SO_2R^7$;

$R^5$ and $R^6$ are independently selected from H, $C_1$–$C_6$ alkyl, $C_3$–$C_{10}$ cycloalkyl, ($C_3$–$C_{10}$ cycloalkyl) $C_1$–$C_6$ alkyl;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each of which is optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that for $SO_2R^7$, $R^7$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl; $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3-C_6$ aminocarbocycle, or $C_2-C_5$ aminoheterocycle;

$R^{13}$ is independently selected at each occurrence from H, $C_1-C_6$ alkyl, $C_3-C_{10}$ cycloalkyl, $(C_3-C_{10}$ cycloalkyl) $C_1-C_6$ alkyl, $C_2-C_6$ alkenyl, $C_2-C_6$ alkynyl, $C_1-C_6$ haloalkyl, with the proviso that for $SO_2R^{13}$, $R^{13}$ cannot be H; and $R^{14}$ is H, $C_1-C_6$ alkyl, $C_3-C_{10}$ cycloalkyl, $(C_3-C_{10}$ cycloalkyl) $C_1-C_6$ alkyl, $C_2-C_4$ alkenyl, $C_2-C_4$ alkynyl, halo, or CN.

11. A compound of the formula

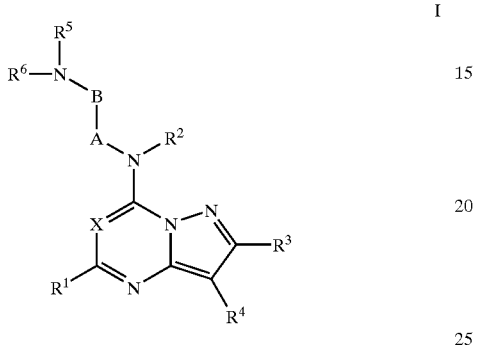

I or a pharmaceutically acceptable salt or an acylated derivative wherein a free hydroxyl or amino group has been acylated to form a compound capable of acting as a prodrug thereof, wherein:

X is $CR^{14}$;

$R^1$ is selected from H, $C_1-C_6$ alkyl, $C_3-C_{10}$ cycloalkyl, $(C_3-C_{10}$ cycloalkyl) $C_1-C_6$ alkyl, $C_2-C_6$ alkenyl, $C_2-C_6$ alkynyl, cyano, halo, $C_1-C_6$ haloalkyl, $OR^7$, $C_1-C_6$ alkyl-$OR^7$, $C_1-C_6$ cyanoalkyl, $NR^8R^9$, and $C_1-C_6$ alkyl-$NR^8R^9$;

$R^2$ is
H,
$C_1-C_6$ alkyl which optionally forms a $C_3-C_6$ aminocarbocycle or a $C_2-C_5$ aminoheterocycle with A or B, each of which is optionally substituted with $R^7$,
$C_3-C_{10}$ cycloalkyl, or
$(C_3-C_{10}$ cycloalkyl) $C_1-C_6$ alkyl; or
$R^2$ and $R^6$ jointly form with the 2 nitrogen atoms to which they are bound a $C_2-C_5$ aminoheterocycle optionally substituted with $R^7$;

A is $(CH_2)_m$ where m is 1,2 or 3 and is optionally mono- or di-substituted at each carbon atom with $C_1-C_6$ alkyl, $C_3-C_{10}$ cycloalkyl, $(C_3-C_{10}$ cycloalkyl) $C_1-C_6$ alkyl, $C_1-C_6$ alkenyl, $C_1-C_6$ alkynyl, cyano, halogen, $C_1-C_6$ haloalkyl, $OR^7$, $C_1-C_6$ alkyl-$OR^7$; $C_1-C_6$ cyanoalkyl, $NR^8R^9$, or $C_1-C_6$ alkyl-$NR^8R^9$, or
A and B jointly form a $C_3-C_6$ carbocycle, which is optionally substituted at each carbon atom with $R^7$, or
A and $R^2$ jointly form a $C_3-C_6$ aminocarbocycle, which is optionally substituted at each carbon atom with $R^7$;

B is $(CH_2)_n$ where n is 0, 1, 2, or 3 and is optionally substituted at each carbon atom with $C_1-C_6$ alkyl, $C_3-C_{10}$ cycloalkyl, $(C_3-C_{10}$ cycloalkyl) $C_1-C_6$ alkyl, $C_2-C_6$ alkenyl, $C_2-C_6$ alkynyl, cyano, halogen, $C_1-C_6$ haloalkyl, $OR^7$, $C_1-C_6$ alkyl-$OR^7$; $C_1-C_6$ cyanoalkyl, $NR^8R^9$, or $C_1-C_6$ alkyl-$NR^8R^9$, or B and $R^2$ jointly form a $C_3-C_6$ aminocarbocycle, which is optionally substituted at each carbon atom with $R^7$, or
B and $R^6$ jointly form a $C_3-C_6$ aminocarbocycle, which is optionally substituted at each carbon atom with $R^7$;

$R^3$ is selected from H, $C_1-C_6$ alkyl, $C_3-C_{10}$ cycloalkyl, $(C_3-C_{10}$ cycloalkyl) $C_1-C_6$ alkyl, $C_2-C_6$ alkenyl, $C_2-C_6$ alkynyl, cyano, halo, $C_1-C_6$ haloalkyl, $OR^7$, $C_1-C_6$ alkyl-$OR^7$, $C_1-C_6$ cyanoalkyl, $NR^8R^9$, and $C_1-C_6$ alkyl-$NR^8R^9$;

$R^4$ is selected from aryl or heteroaryl, each substituted with aryl, heteroaryl, heterocycloalkyl, and 3-, 4-, or (5-(2-oxo-1,3-oxazolidinyl), heterocycloalkyl, cyclopentenyl, cyclohexenyl, $C_1-C_6$ alkenyl, $C_1-C_6$ alkynyl, $(C_3-C_{10}$ cycloalkyl)$C_1-C_6$ alkyl, trifluoromethylsulfonyl, $C_1-C_6$ alkyl-$NR^8R^9$, $C_1-C_6$ alkyl-CN, $C_1-C_6$ alkyl-$CONR^8R^9$, $C_1-C_6$ alkyl-$OR^7$, $C_1-C_6$ alkyl-$COOR^7$ and optionally substituted with 1 to 4 substituents independently selected at each occurrence from $C_1-C_6$ alkyl, $(C_3-C_{10}$ cycloalkyl) $C_1-C_6$ alkyl, halogen, $C_1-C_6$ haloalkyl, trifluoromethylsulfonyl, $OR^7$, $C_1-C_6$ alkyl-$OR^7$, $NR^8R^9$, $C_1-C_6$alkyl-$NR^8R^9$, $CONR^8R^9$, $C_1-C_6$ alkyl-$CONR^8R^9$, $COOR^7$, $C_1-C_6$ alkyl-$COOR^7$, CN, $C_1-C_6$ alkyl-CN, $SO_2NR^8R^9$, $SO_2R7$;

$R^5$ and $R^6$ are independently selected from H, $C_1-C_6$ alkyl, $C_3-C_{10}$ cycloalkyl, $(C_3-C_{10}$ cycloalkyl) $C_1-C_6$ alkyl;

$R^7$ is H, $C_1-C_6$ alkyl, $C_3-C_{10}$ cycloalkyl, $C_3-C_{10}$ cycloalkenyl, $(C_3-C_{10}$ cycloalkyl) $C_1-C_6$ alkyl, $C_1-C_3$ haloalkyl, or heterocycloalkyl, $C_1-C_8$ alkylsulfonyl, arylsulfonyl, heteroarylsulfonyl, $C_1-C_8$ alkanoyl, aroyl, heteroaroyl, aryl, heteroaryl, $C_1-C_6$ arylalkyl or $C_1-C_6$ heteroarylalkyl each of which is optionally substituted with 1 to 5 substituents independently selected at each occurrence from halogen, $C_1-C_6$ haloalkyl, $OR^{13}$, $NR^8R^9$, $C_1-C_6$ alkyl-$OR^{13}$, $C_1-C_6$ alkyl-$NR^8R^9$, $CONR^8R^9$, $COOR^{13}$, CN, $SO_2NR^8R^9$, $SO_2R^{13}$, with the proviso that when $R^7$ is $SO_2R^{13}$, $R^{13}$ cannot be H;

$R^8$ and $R^9$ are independently selected at each occurrence from H, $C_1-C_6$ alkyl, $C_3-C_{10}$ cycloalkyl, $C_2-C_6$ alkenyl, $C_3-C_{10}$ cycloalkenyl, $C_2-C_6$ alkynyl, heterocycloalkyl, $C_1-C_8$ alkanoyl, aroyl, heteroaroyl, aryl, heteroaryl, $C_1-C_6$ arylalkyl or $C_1-C_6$ heteroarylalkyl, or $R^8$ and $R^9$, taken together, can form a $C_3-C_6$ aminocarbocycle or a $C_2-C_5$ aminoheterocycle each optionally substituted at each occurrence with $C_1-C_6$ alkyl, $C_3-C_{10}$ cycloalkyl, $C_3-C_{10}$ cycloalkenyl, $(C_3-C_{10}$ cycloalkyl) $C_1-C_6$ alkyl, $C_1-C_3$ haloalkyl, or heterocycloalkyl, $C_1-C_8$ alkylsulfonyl, arylsulfonyl, heteroarylsulfonyl, $C_1-C_8$ alkanoyl, aroyl, heteroaroyl, aryl, heteroaryl, $C_1-C_6$ arylalkyl or $C_1-C_6$ heteroarylalkyl;

$R^{11}$ is selected from H, $C_1-C_6$ alkyl, $C_3-C_{10}$ cycloalkyl, $(C_3-C_{10}$ cycloalkyl) $C_1-C_6$ alkyl;

$R^{12}$ is selected from H, aryl, heteroaryl, $C_1-C_6$ alkyl, $C_3-C_{10}$ cycloalkyl, $(C_3-C_{10}$ cycloalkyl) $C_1-C_6$ alkyl, optionally substituted with $OR^7$, $NR^8R^9$, $C_3-C_6$ aminocarbocycle, or $C_2-C_5$ aminoheterocycle;

$R^{13}$ is independently selected at each occurrence from H, $C_1-C_6$ alkyl, $C_3-C_{10}$ cycloalkyl, $(C_3-C_{10}$ cycloalkyl) $C_1-C_6$ alkyl, $C_2-C_6$ alkenyl, $C_2-C_6$ alkynyl, $C_1-C_6$ haloalkyl, with the proviso that for $SO_2R^{13}$, $R^{13}$ cannot be H; and $R^{14}$ is H, $C_1-C_6$ alkyl, $C_3-C_{10}$ cycloalkyl, $(C_3-C_{10}$ cycloalkyl) $C_1-C_6$ alkyl, $C_2-C_4$ alkenyl, $C_2-C_4$ alkynyl, halo, or CN.

12. A compound according to claim 10, wherein
X is CH;
$R^1$ is H, $C_1-C_6$ alkyl, $C_3-C_{10}$ cycloalkyl, or $(C_3-C_{10}$ cycloalkyl) $C_1C_1-C_6$ alkyl;

$R^2$ is H;

$R^3$ is $C_1$–$C_6$ alkyl, trifluoromethyl, or $C_1$–$C_6$alkyl-O $C_1$–$C_6$alkyl;

$R^4$ is phenyl, mono-, di-, or tri-substituted $C_1$–$C_6$ alkyl, halogen, $C_1$–$C_6$ haloalkyl, or $OR^7$;

$R^5$ is H;

$R^7$ is methyl, ethyl, isopropyl, or propyl.

13. A compound of claim 12 wherein the compound has the structure N-cyclohexyl-N'-[3-(2,6-dichloro-4-methoxy-phenyl)-2,5-dimethyl-pyrazolo[1,5-a]pyrimidin-7-yl]-ethane-1,2-diamine; N-cyclohexyl-N'-[2,5-dimethyl-3-(2,4,6-trimethyl-phenyl)-pyrazolo[1,5-a]pyrimidin-7-yl]-ethane-1,2-diamine; N-cCyclopentyl-N'-[2,5-dimethyl-3-(2,4,6-trimethyl-phenyl)-pyrazolo[1,5-a]pyrimidin-7-yl]-ethane-1,2-diamine; or N-cyclopentyl-N'-[3-(2,6-dichloro-4-methoxy-phenyl)-2,5-dimethyl-pyrazolo [1,5-a]pyrimidin-7-yl]-ethane-1,2-diamine.

14. A compound according to claim 11, wherein $R^{14}$ is H, $C_1$–$C_4$ alkyl.

15. A compound according to claim 14 wherein $R^2$ is H; $R^6$ is H;

X is CH;

A is $CH_2$, optionally substituted with one or two of the following: F, $CF_3$, or methyl, ethyl, isopropyl;

B is $CH_2$, optionally substituted with one or two of the following: F, $CF_3$, or methyl, ethyl, isopropyl.

16. A compound according to claim 15 wherein $R^5$ is $C_1$–$C_7$ alkyl, $C_1$–$C_6$ cycloalkyl, or $C_1$–$C_6$ cycloalkyl $C_1$–$C_2$ alkyl;

A, B is $CH_2$.

17. A compound according to claim 15 wherein $R^4$ is selected from aryl or heteroaryl, each substituted with aryl, heteroaryl, heterocycloalkyl, and 3-, 4-, or 5-(2-oxo-1,3-oxazolidinyl), heterocycloalkyl, cyclopentenyl, cyclohexenyl, $C_1$–$C_6$ alkenyl, $C_1$–$C_6$ alkynyl, ($C_3$–$C_{10}$ cycloalkyl) $C_1$–$C_6$ alkyl, trifluoromethylsulfonyl, $C_1$–$C_6$ alkyl-$NR^8R^9$, $C_1$–$C_6$ alkyl-CN, $C_1$–$C_6$ alkyl-$CONR^8R^9$, ($C_1$–$C_4$)alkyl-$OR^7$, $C_1$–$C_6$ alkyl-$COOR^7$ and optionally substituted with 1 to 4 substituents independently selected at each occurrence from $C_1$–$C_6$ alkyl, ($C_3$–$C_{10}$ cycloalkyl) $C_1$–$C_6$ alkyl, halogen, $C_1$–$C_6$ haloalkyl, trifluoromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl.

18. A compound of claim 17 wherein $R^4$ is phenyl substituted with acetylene, cyclopentenyl, cyclohexenyl, ($C_1$–$C_4$)alkyl-$OR^7$, $C_1$–$C_3$ alkenyl, and optionally substituted with 1 to 2 substituents independently selected at each occurrence from methyl, F, Cl, $CF_3$, $OR^7$;

$R^7$ is H, methyl, ethyl.

19. A compound of claim 18 where the structure is N-cyclohexyl-N'-[3-(2,6-dichloro-4-ethynyl-phenyl)-2,5-dimethyl-pyrazolo[1,5-a]pyrimidin-7yl]-ethane-1,2-diamine; N-cyclopentyl-N'-[3-(2,6-dichloro-4-ethynyl-phenyl)-2,5-dimethyl-pyrazolo[1,5-a]pyrimidin-7-yl]-ethane-1,2-diamine; N-cyclopentyl-N'-[3-(2,6-dichloro-4-cyclopent-1-enyl-phenyl)-2,5-dimethyl-pyrazolo[1,5-a]pyrimidin-7-yl]-ethane-1,2-diamine; or N-cyclohexyl-N'-[3-(2,6-dichloro-4-cyclopent-1-enyl-phenyl)-2,5-dimethyl-pyrazolo[1,5-a]pyrimidin-7-yl]-ethane-1,2-diamine.

20. A compound according to claim 10 wherein the compound exhibits a 20-fold greater affinity for the NPY1 receptor in the NPY1 receptor binding assay than for the CRF receptor in an assay of CRF receptor as determined by binding to a radiolabeled ligand.

21. A compound according to claim 10 wherein the compound exhibits a 100-fold greater affinity for the NPY1 receptor in the NPY1 receptor binding assay than for the CRF receptor in an assay of CRF receptor as determined by binding to a radiolabeled ligand.

22. A method for treating eating disorders comprising administering to a patient suffering from an eating disorder a compound according to claim 10.

23. A pharmaceutical composition comprising a compound according to claim 10 and a pharmaceutically acceptable carrier.

24. A packaged pharmaceutical composition comprising the pharmaceutical composition of claim 10 in a container and comprising instructions for using the composition to treat a patient suffering from an eating disorder or hypertension.

25. A method for treating obesity or bulimia nervosa which comprises administering an effective amount of a compound according to claim 10 to a patient in need thereof.

26. A method of treating obesity comprising administering to a mammal in need of such treatment a therapeutically effective amount of a compound of formula as defined in claim 11 or a prodrug thereof or a pharmaceutically acceptable salt of said compound or of said prodrug.

27. A method as recited in claim 26 wherein the amount of the compound in Formula I as defined in claim 11 is about 0.01 mg/kg/day to about 50 mg/kg/day.

28. A method as recited in claim 27 wherein the mammal is female or male human.

29. A pharmaceutical composition which comprises a therapeutically effective amount of compound of claim 11 or a prodrug thereof or a pharmaceutically acceptable salt of said compound or of said prodrug and a pharmaceutically acceptable carrier, vehicle or diluent.

30. A pharmaceutical composition for the treatment of obesity which comprises a therapeutically effective amount of compound of claim 11 or a prodrug thereof or a pharmaceutically acceptable salt of said compound or of said prodrug and a pharmaceutically acceptable carrier, vehicle or diluent.

31. A pharmaceutical composition comprising a compound as defined in claim 11 and a pharmaceutically acceptable carrier for the treatment of disorders or disease states caused by eating disorders, of obesity, bulimia nervosa, dislipidemia, memory loss, epileptic seizures, migraine, sleep disorders, pain, sexual/reproductive disorders, depression, anxiety, cerebral hemorrhage, shock, nasal congestion or diarrhea.

* * * * *

SEQUENCE LISTING

<160> NUMBER OF SEQ ID NOS: 1

<210> SEQ ID NO 1
<211> LENGTH: 1605
<212> TYPE: DNA
<213> ORGANISM: Homo sapiens

<400> SEQUENCE: 1

```
ccttctttaa tgaagcagga gcgaaaaaga caaattccaa agaggattgt t cagttcaag     60 ggaatgaaga attcagaata attttggtaa atggattcca atatggggaa t aagaataag    120 ctgaacagtt gacctgcttt gaagaaacat actgtccatt tgtctaaaat a atctataac    180 aaccaaacca atcaaaatga attcaacatt attttcccag gttgaaaatc a ttcagtcca    240 ctctaatttc tcagagaaga atgcccagct tctggctttt gaaaatgatg a ttgtcatct    300 gcccttggcc atgatattta ccttagctct tgcttatgga gctgtgatca t tcttggtgt    360 ctctggaaac ctggccttga tcataatcat cttgaaacaa aaggagatga g aaatgttac    420 caacatcctg attgtgaacc tttccttctc agacttgctt gttgccatca t gtgtctccc    480 ctttacattt gtctacacat taatggacca ctgggtcttt ggtgaggcga t gtgtaagtt    540 gaatccttttt gtgcaatgtg tttcaatcac tgtgtccatt ttctctctgg t tctcattgc    600 tgtggaacga catcagctga taatcaaccc tcgagggtgg agaccaaata a tagacatgc    660 ttatgtaggt attgctgtga tttgggtcct tgctgtggct tcttctttgc c tttcctgat    720 ctaccaagta atgactgatg agccgttcca aaatgtaaca cttgatgcgt a caaagacaa    780 atacgtgtgc tttgatcaat ttccatcgga ctctcatagg ttgtcttata c cactctcct    840 cttggtgctg cagtattttg gtccactttg ttttatattt atttgctact t caagatata    900 tatacgccta aaaggagaa acaacatgat ggacaagatg agagacaata a gtacaggtc    960 cagtgaaacc aaaagaatca atatcatgct gctctccatt gtggtagcat t tgcagtctg   1020 ctggctccct cttaccatct ttaacactgt gtttgattgg aatcatcaga t cattgctac   1080 ctgcaaccac aatctgttat tcctgctctg ccacctcaca gcaatgatat c cacttgtgt   1140 caaccccata ttttatgggt tcctgaacaa aaacttccag agagacttgc a gttcttctt   1200 caactttttgt gatttccggt ctcgggatga tgattatgaa acaatagcca t gtccacgat   1260
```

-continued

```
gcacacagat gtttccaaaa cttctttgaa gcaagcaagc ccagtcgcat t taaaaaaat  1320 caacaacaat gatgataatg aaaaaatctg aaactactta tagcctatgg t cccggatga  1380 catctgttta aaaacaagca caacctgcaa catactttga ttacctgttc t cccaaggaa  1440 tggggttgaa atcatttgaa aatgactaag attttcttgt cttgcttttt a ctgcttttg  1500 ttgtagttgt cataattaca tttggaacaa aaggtgtggg ctttggggtc t tctggaaat  1560 agttttgacc agacatcttt gaagtgcttt ttgtgaattt accag                   1605
```